(12) United States Patent
Sui et al.

(10) Patent No.: US 6,831,742 B1
(45) Date of Patent: Dec. 14, 2004

(54) MONITORING SUBSTRATE PROCESSING USING REFLECTED RADIATION

(75) Inventors: Zhifeng Sui, Milpitas, CA (US); Hongqing Shan, Cupertino, CA (US); Nils Johansson, Los Gatos, CA (US); Hamid Noorbakhsh, Fremont, CA (US); Yu Guan, San Jose, CA (US)

(73) Assignee: Applied Materials, Inc, Santa Clara, CA (US)

(*) Notice: Subject to any disclaimer, the term of this patent is extended or adjusted under 35 U.S.C. 154(b) by 610 days.

(21) Appl. No.: 09/695,577

(22) Filed: Oct. 23, 2000

(51) Int. Cl.$^7$ .................................................. G01J 4/00
(52) U.S. Cl. ...................... 356/369; 356/364; 356/630; 438/700; 216/2
(58) Field of Search ................................ 356/369, 364, 356/630; 250/225; 438/700, 701, 710, 14, 16; 216/2

(56) References Cited

U.S. PATENT DOCUMENTS

| | | |
|---|---|---|
| 3,170,383 A | 2/1965 | d'A.Hunt |
| 3,316,468 A | 4/1967 | Hanks |

(List continued on next page.)

FOREIGN PATENT DOCUMENTS

| | | |
|---|---|---|
| EP | 607797 A1 | 7/1994 |
| EP | 756318 A1 | 1/1997 |
| EP | 801413 A1 | 10/1997 |
| EP | 818814 A2 | 1/1998 |
| EP | 818814 A3 | 2/1999 |
| EP | 908922 A1 | 4/1999 |
| GB | 0202808 A | 11/1979 |
| JP | 4260017 | 9/1962 |
| JP | 61160926 | 7/1986 |
| JP | 63253617 | 10/1988 |
| JP | 6471122 | 3/1989 |
| JP | 1126529 | 5/1989 |
| JP | 3015198 | 1/1991 |
| JP | 4278446 | 10/1992 |
| JP | 7006948 | 1/1995 |
| JP | 7103906 | 4/1995 |
| JP | 8211297 | 8/1996 |
| JP | 7280020 | 5/1997 |
| JP | 10-239028 | 9/1998 |
| JP | 11077525 | 3/1999 |
| WO | 9733158 | 9/1997 |
| WO | 9830866 | 7/1998 |
| WO | 9832153 | 7/1998 |
| WO | 9833055 | 7/1998 |
| WO | 9844535 | 10/1998 |
| WO | 9845869 | 10/1998 |
| WO | 9848444 | 10/1998 |
| WO | 9914791 | 3/1999 |
| WO | 9944052 | 9/1999 |
| WO | 9945340 | 9/1999 |
| WO | 9951955 | 10/1999 |
| WO | 0020841 | 4/2000 |
| WO | 00047961 | 8/2000 |

OTHER PUBLICATIONS

Biolsi, P. et al., "An Advanced Endpoint Detection Solution for <1% Open Areas", Solid State Technology, vol. 39, No. 12, Dec. 1, 1996, pp. 59, 61–62, 64, 67.
PCT Search Report for International Application No. PCT/US01/49437, dated Apr. 9, 2003.

*Primary Examiner*—Frank G. Font
*Assistant Examiner*—Roy M. Punnoose
(74) *Attorney, Agent, or Firm*—Ashok K. Janah; Joseph Bach

(57) ABSTRACT

A substrate processing apparatus 27 comprises a chamber 35 capable of processing a substrate 20, a radiation source 58 to provide a radiation, a radiation polarizer 59 adapted to polarize the radiation to one or more polarization angles that are selected in relation to an orientation 33 of a feature 25 being processed on the substrate 20, a radiation detector 54 to detect radiation reflected from the substrate 20 during processing and generate a signal, and a controller 100 to process the signal.

99 Claims, 15 Drawing Sheets

U.S. PATENT DOCUMENTS

| | | |
|---|---|---|
| 4,037,945 A | 7/1977 | Wollam |
| 4,175,441 A | 11/1979 | Urbanek et al. |
| 4,208,240 A | 6/1980 | Latos |
| 4,280,354 A | 7/1981 | Wheeler et al. |
| 4,302,721 A | 11/1981 | Urbanek et al. |
| 4,532,650 A | 7/1985 | Wihl et al. |
| 4,555,798 A | 11/1985 | Broadbent, Jr. et al. |
| 4,758,094 A | 7/1988 | Wihl et al. |
| 4,844,617 A | 7/1989 | Kelderman et al. |
| 4,889,676 A | 12/1989 | Rosenberg et al. |
| 4,898,471 A | 2/1990 | Vaught et al. |
| 4,899,055 A | 2/1990 | Adams |
| 4,998,019 A | 3/1991 | Stokowski et al. |
| 5,014,627 A | 5/1991 | Rosenberg et al. |
| 5,026,437 A | 6/1991 | Neukermans et al. |
| 5,030,008 A | 7/1991 | Scott et al. |
| 5,074,985 A | 12/1991 | Tamura et al. |
| 5,112,129 A | 5/1992 | Davidson et al. |
| 5,129,994 A | 7/1992 | Ebbing et al. |
| 5,131,752 A | 7/1992 | Yu et al. |
| 5,160,402 A | 11/1992 | Cheng |
| 5,166,751 A | 11/1992 | Massig |
| 5,225,888 A | 7/1993 | Selwyn et al. |
| 5,241,366 A | 8/1993 | Bevis et al. |
| 5,248,889 A | 9/1993 | Blech et al. |
| 5,257,092 A | 10/1993 | Noguchi et al. |
| 5,277,746 A | 1/1994 | Anderson |
| 5,290,383 A | 3/1994 | Koshimuzu |
| 5,370,765 A | 12/1994 | Dandl |
| 5,392,116 A | 2/1995 | Makosch |
| 5,416,594 A | 5/1995 | Gross et al. |
| 5,459,570 A | 10/1995 | Swanson et al. |
| 5,531,862 A | 7/1996 | Otsubo et al. |
| 5,552,704 A | 9/1996 | Mallory et al. |
| 5,572,598 A | 11/1996 | Wihl et al. |
| 5,581,350 A | 12/1996 | Chen et al. |
| 5,608,526 A | 3/1997 | Piwonka-Corle et al. |
| 5,622,635 A | 4/1997 | Cuomo et al. |
| 5,643,364 A | 7/1997 | Zhao et al. |
| 5,665,968 A | 9/1997 | Meisburger et al. |
| 5,717,204 A | 2/1998 | Meisburger et al. |
| 5,738,756 A | 4/1998 | Liu |
| 5,800,688 A | 9/1998 | Lantsman et al. |
| 5,889,593 A | 3/1999 | Bareket |
| 5,936,734 A | 8/1999 | Johs et al. |
| 6,006,694 A | 12/1999 | DeOrnellas et al. |
| 6,052,183 A | 4/2000 | Lee |
| 6,066,849 A | 5/2000 | Masnaghetti et al. |
| 6,079,256 A | 6/2000 | Bareket |
| 6,081,334 A * | 6/2000 | Grimbergen et al. ....... 356/499 |
| 6,090,717 A | 7/2000 | Powell et al. |
| 6,406,924 B1 * | 6/2002 | Grimbergen et al. .......... 439/9 |

* cited by examiner

MONITORING SUBSTRATE PROCESSING USING REFLECTED RADIATION

BACKGROUND

The invention relates to monitoring the processing of a substrate.

In substrate processing methods, features comprising semiconductor, dielectric, and conductor materials, including but not limited to, silicon, polysilicon, silicon dioxide, aluminum, copper and tungsten silicide materials, are formed on a substrate by, for example, chemical vapor deposition (CVD), physical vapor deposition (PVD), oxidation, nitridation, ion implantation, and etching processes. In CVD processes, a reactive gas is used to deposit material on the substrate. In PVD processes, a target is sputtered to deposit material on the substrate. In oxidation and nitridation processes, an oxide or nitride material, such as silicon dioxide or silicon nitride, is formed on the substrate by exposing the substrate to a suitable gaseous environment. In ion implantation, ions are implanted into the substrate, In conventional etching processes, etch-resistant features comprising resist or hard-mask, are formed on the substrate and the exposed portions of the substrate between the etch-resistant features (substrate open area) are etched to form patterns of gates, vias, contact holes or interconnect lines.

Conventional methods of monitoring the processing of a substrate or of a process conducted in a substrate processing chamber often have problems. The process monitoring methods may be used to stop or change the process, for example, after a pre-determined change occurs in a feature or material being processed, after a process stage, or at a process endpoint. For example, in the etching of trenches in a dielectric, such as silicon dioxide, on a silicon wafer, it may be desirable to stop etching after reaching a predetermined depth. In one conventional method, the time required to etch a particular depth in a substrate is calculated from a predetermined rate of etching and a starting thickness of the substrate layer or material being etched. In another method, the peaks resulting from the constructive and destructive interference of radiation reflected from the substrate are counted to determine a substrate etching depth. However, such techniques are often inaccurate when the starting thickness of the material on the substrate varies from one substrate to another or when other process parameters change. It is especially difficult to accurately monitor an etching process when the substrate being etched has a small open area between the etch-resistant features because the process signal from such a region is small relative to the process signal from other portions of the substrate. It is also difficult to determine the depth of a material deposited within a via or trench on the substrate, for example, during the deposition of dielectric or metal material into a via or trench, because of the small area of the deposited material.

Thus, it is desirable to detect a small change that may occur during processing of a substrate. It is also desirable to quantitatively evaluate the change, for example, a depth of etching, or a thickness of the material deposited upon, the substrate. It is further desirable to accurately monitor substrate processing during the etching of a substrate having small open areas or during the deposition of material into small areas on the substrate.

SUMMARY

The present invention satisfies these needs. In one aspect, the present invention comprises a substrate processing apparatus comprising a chamber capable of processing a substrate, a radiation source to provide a radiation, a radiation polarizer adapted to polarize the radiation to one or more polarization angles that are selected in relation to an orientation of a feature being processed on the substrate, a radiation detector to detect radiation reflected from the substrate during processing and generate a signal, and a controller to process the signal.

In another aspect, the invention comprises a method of processing a substrate in a process zone, the method comprising the steps of providing a substrate in the process zone, setting process conditions to process the substrate with an energized gas, providing radiation that is polarized at one or more polarization angles that are selected in relation to an orientation of a feature being processed on the substrate, detecting radiation reflected from the substrate and generating a signal in response to the detected radiation, and processing the signal.

In yet another aspect, the invention comprises a substrate processing apparatus comprising a chamber capable of processing a substrate, a radiation source to provide a radiation, a radiation polarizer adapted to polarize the radiation to a plurality of polarization angles, a radiation detector to detect radiation reflected from the substrate during processing and generate a signal, and a controller to process the signal.

In a further aspect, the invention comprises a method of processing a substrate in a process zone, the method comprising the steps of providing a substrate in the process zone, setting process conditions to process a feature on the substrate with an energized gas, providing radiation that is polarized to a plurality of polarization angles, detecting radiation reflected from the substrate and generating a signal in response to the detected radiation, and processing the signal.

In another aspect, the invention comprises a substrate processing apparatus comprising a chamber capable of processing a substrate, a radiation source to provide a radiation, a radiation detector to detect radiation reflected from the substrate during processing and generate a signal, and a bandpass filter to filter the signal.

In another aspect, the invention comprises a substrate processing method comprising placing a substrate in a process zone, setting process conditions of an energized gas to process the substrate, providing a source of radiation in the process zone, detecting radiation that is reflected from a substrate during processing of the substrate and generating a signal, and filtering the signal.

In another aspect, the present invention comprises a substrate processing apparatus comprising a process chamber comprising a substrate support, gas inlet, gas energizer, gas exhaust, and a wall having a recess with a window therein and a mask over the window, and a process monitoring system capable of monitoring a process that may be conducted in the process chamber, through the window in the recess of the wall.

In a further aspect, the present invention comprises a method of processing a substrate in a chamber, the method comprising, placing the substrate in the chamber, providing an energized gas in the chamber to process the substrate, masking a window provided in a recess in a wall of the chamber, and monitoring a process that may be conducted in the chamber through the window in the recess in the wall.

DRAWINGS

These and other features, aspects, and advantages of the present invention will be better understood from the following drawings, description and appended claims, which illustrate examples of the invention. However, it is to be understood that each of the features can be used in the invention in general, not merely in the context of a particular drawing, and the invention includes any combination of these features.

Figure 5A:
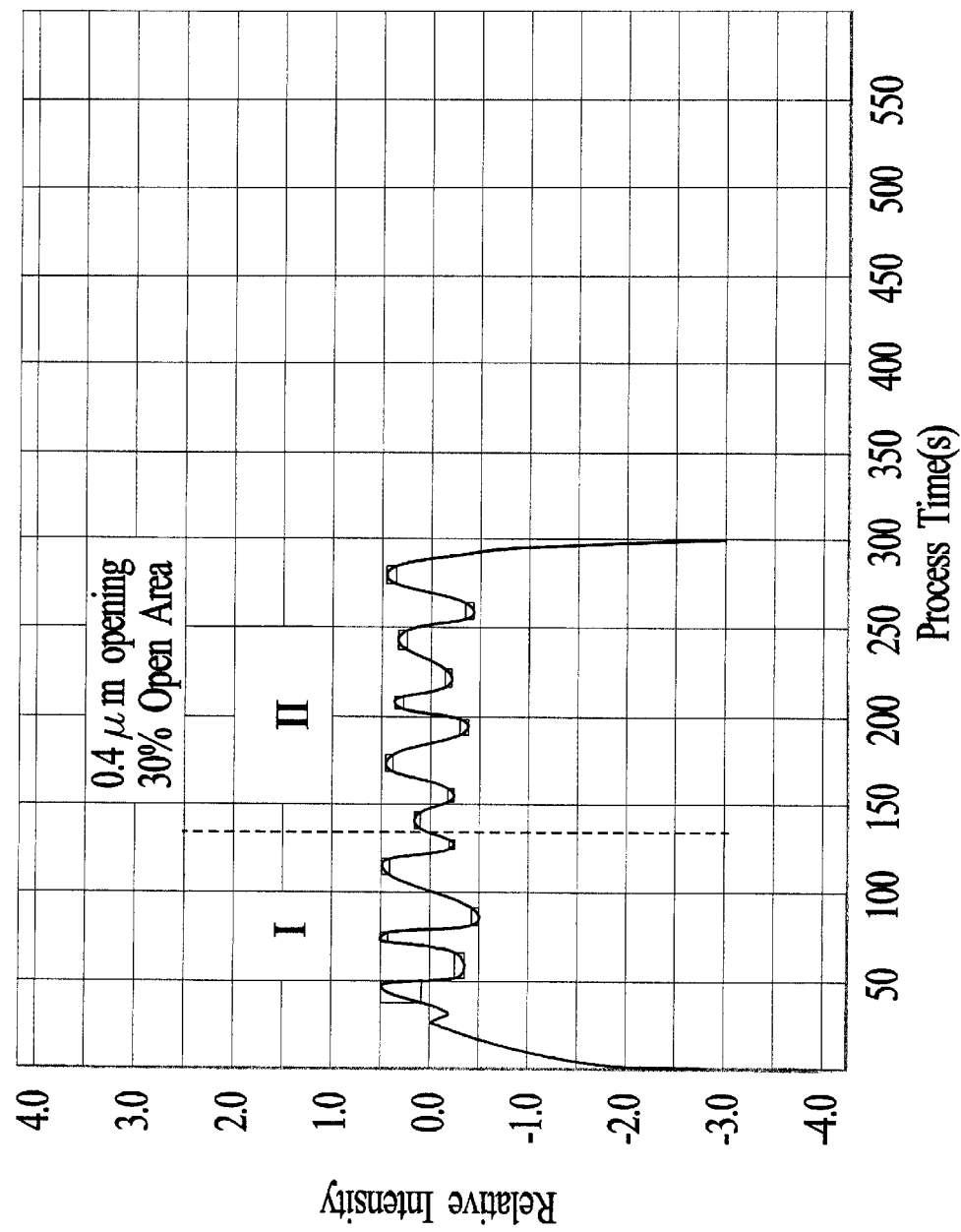
Figure 5B:
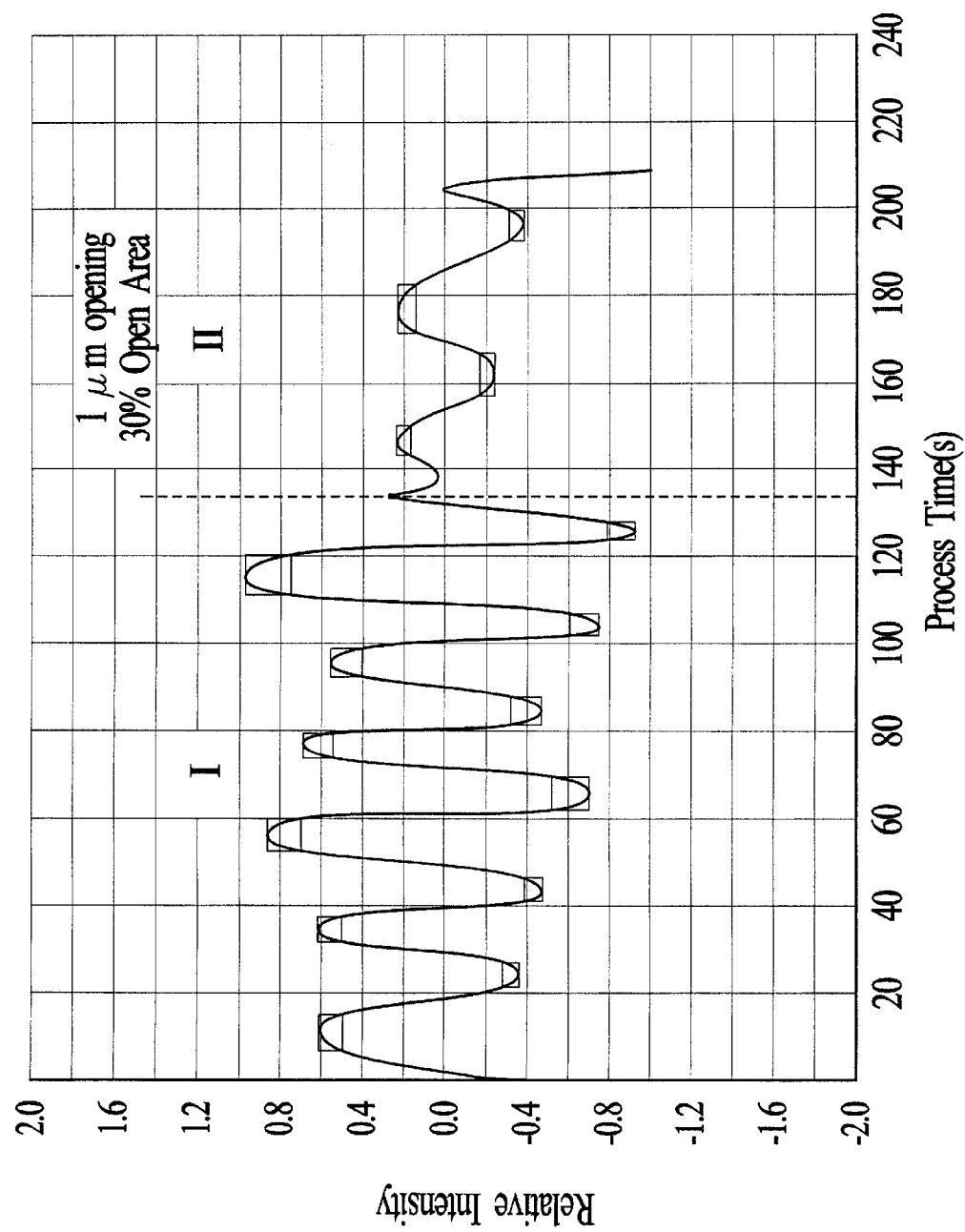
Figure 6:
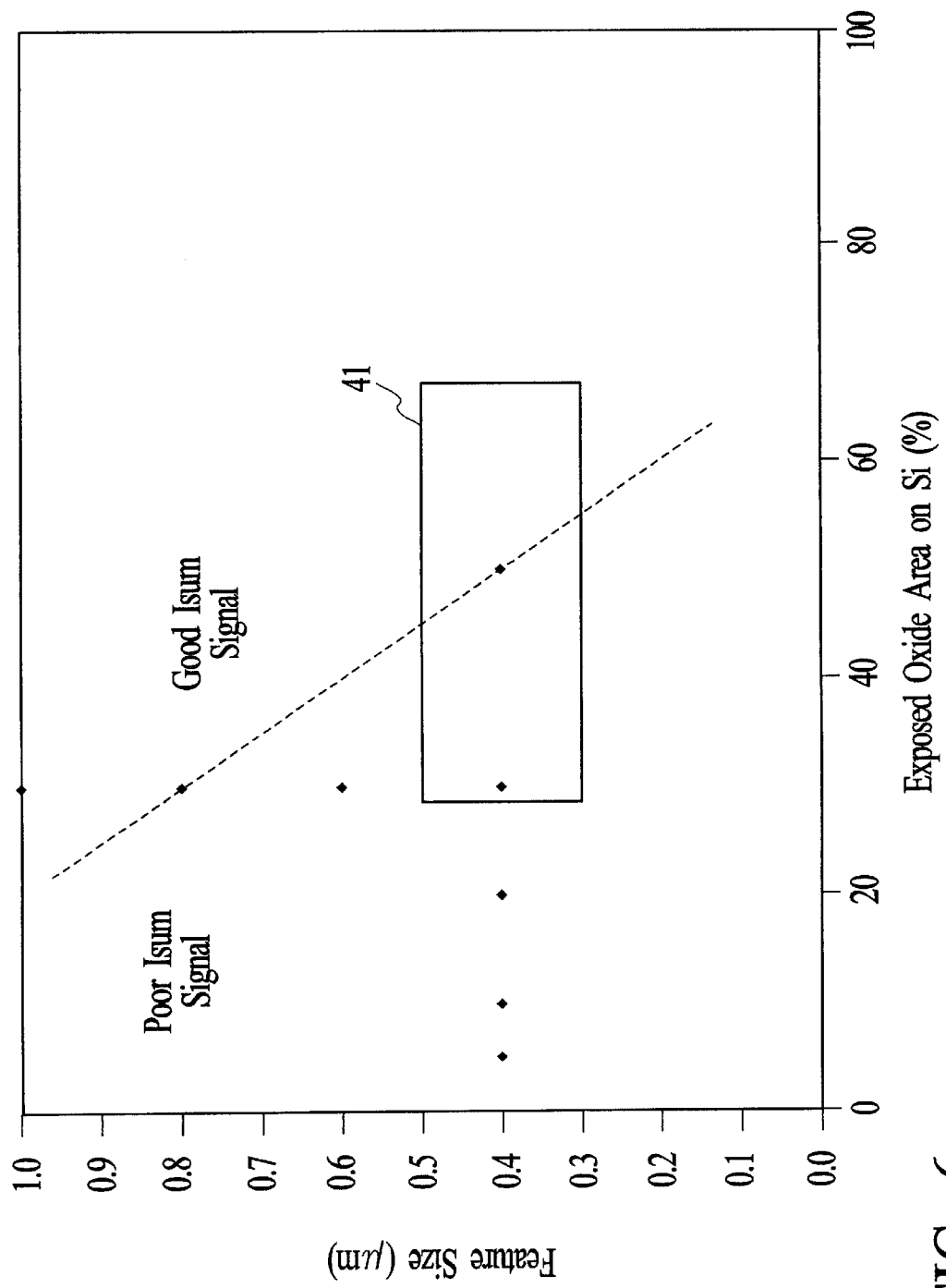
Figure 7:
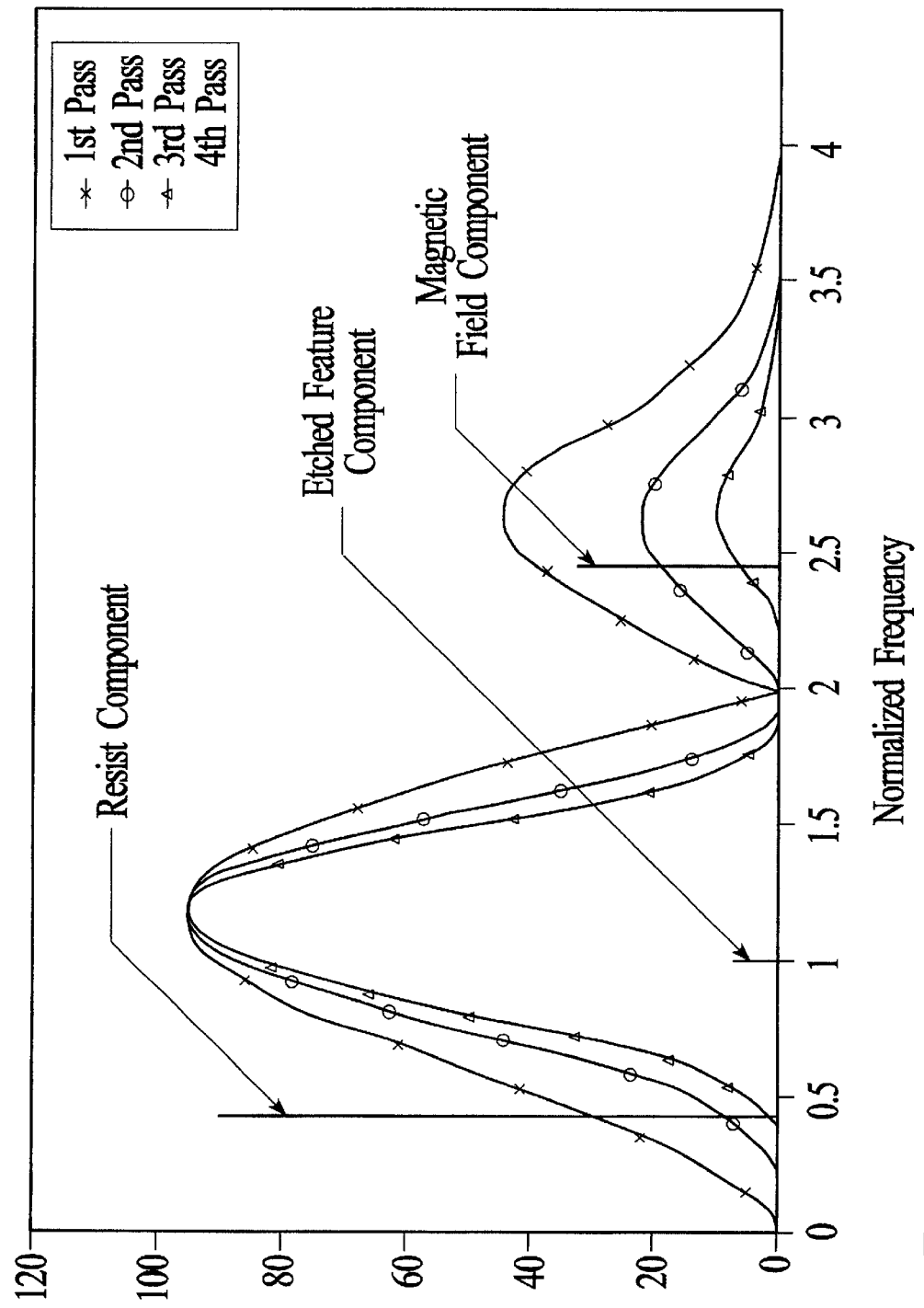
Figure 8A:
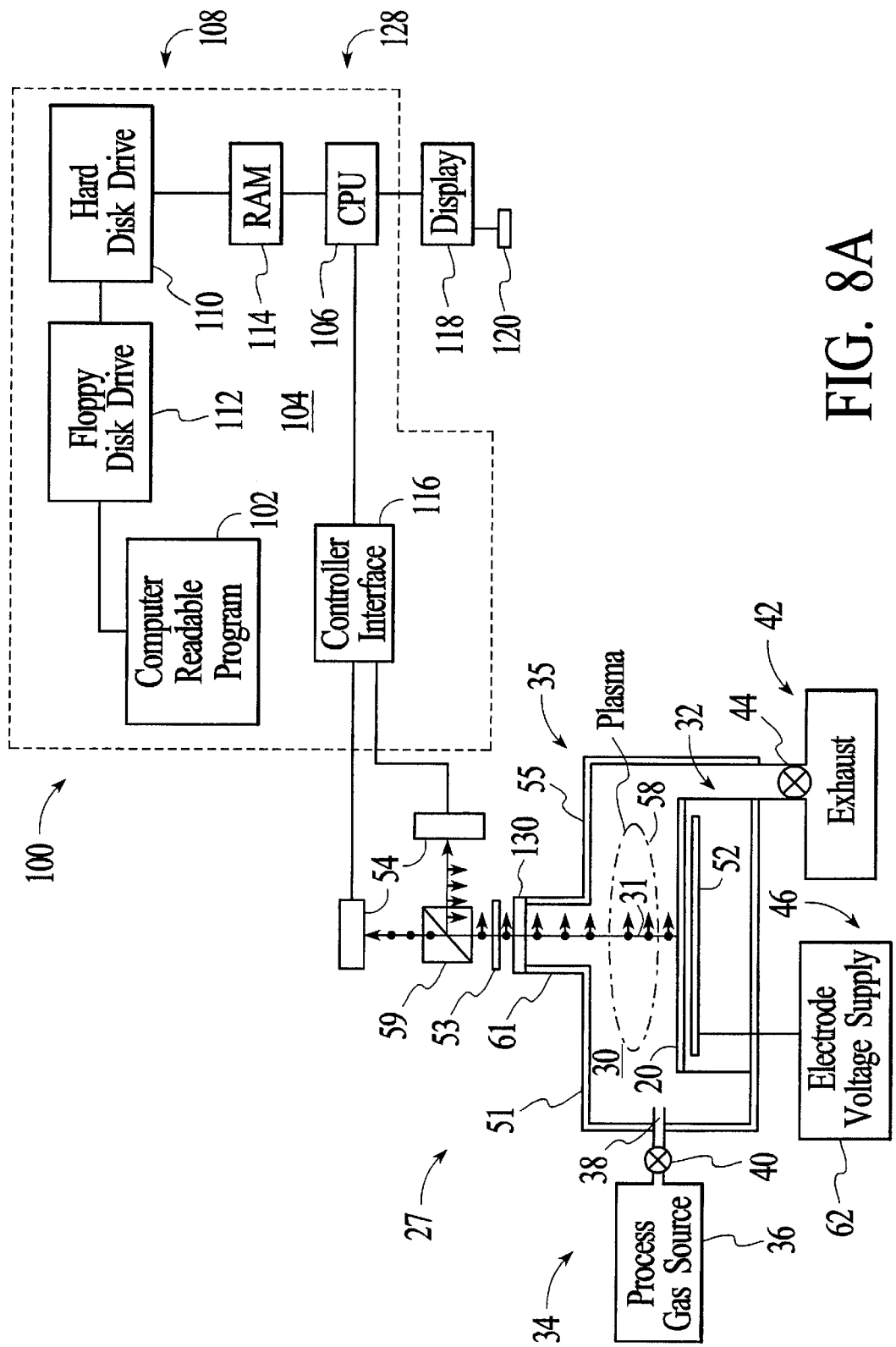
Figure 8B:
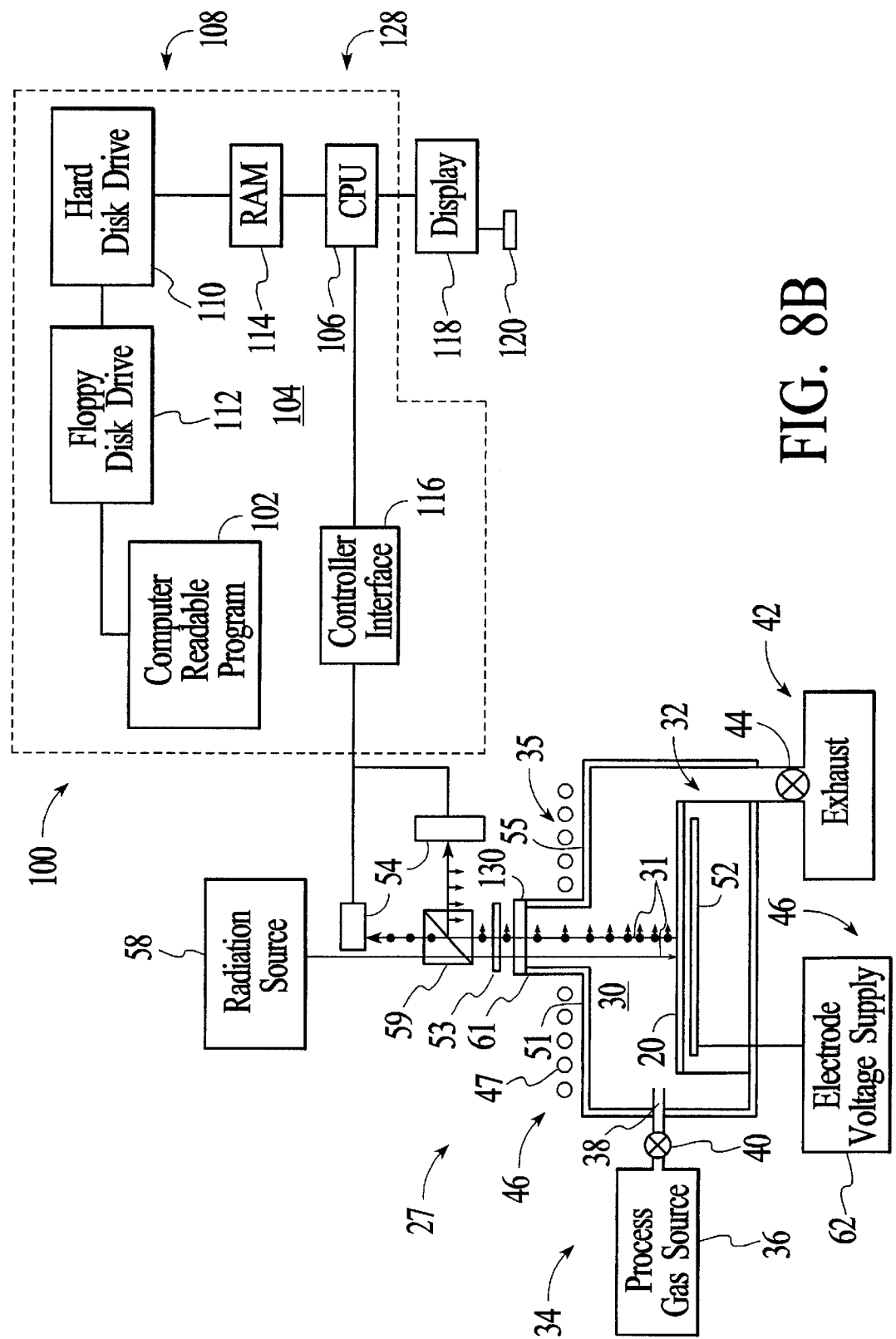
Figure 9:
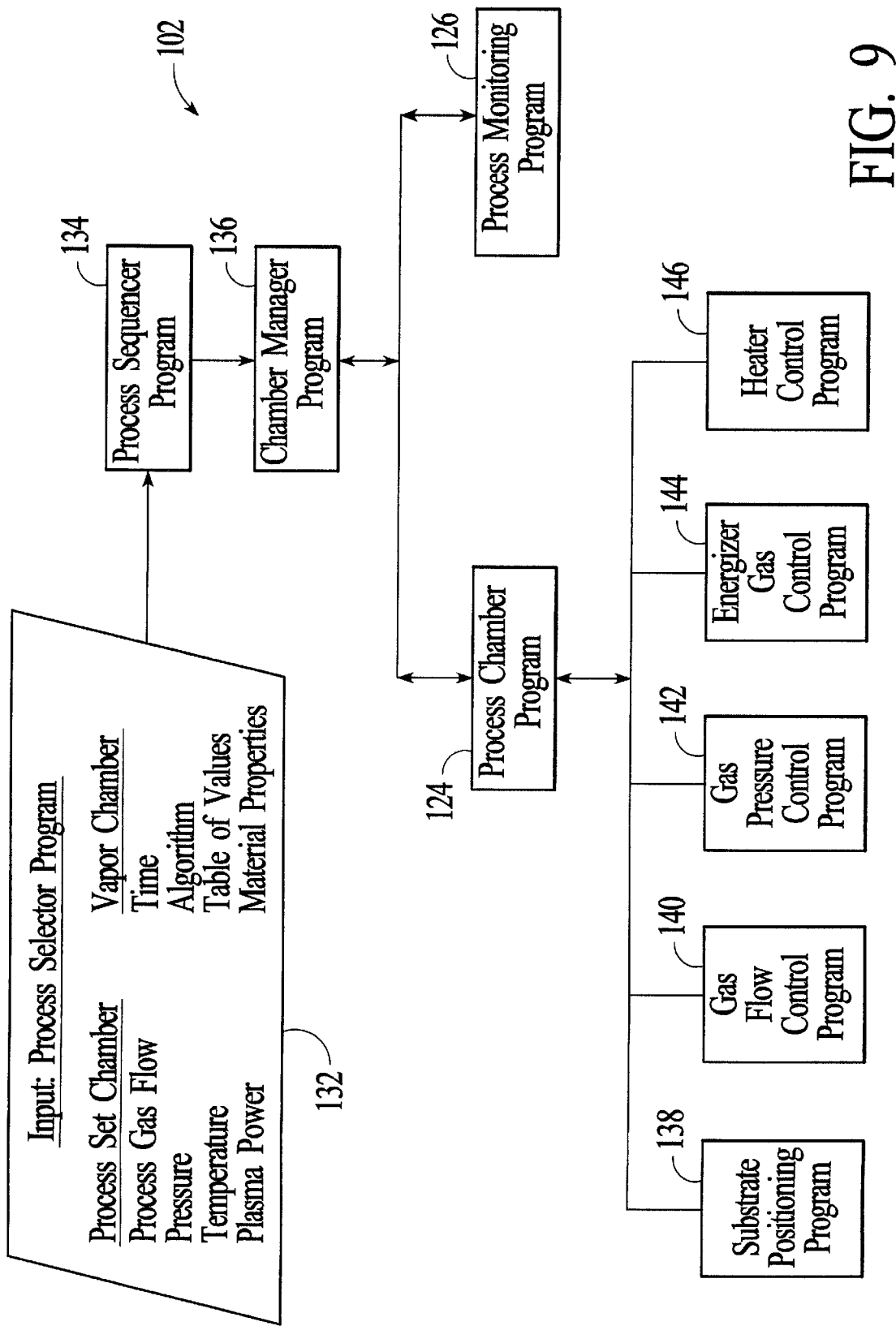
Figure 10A:
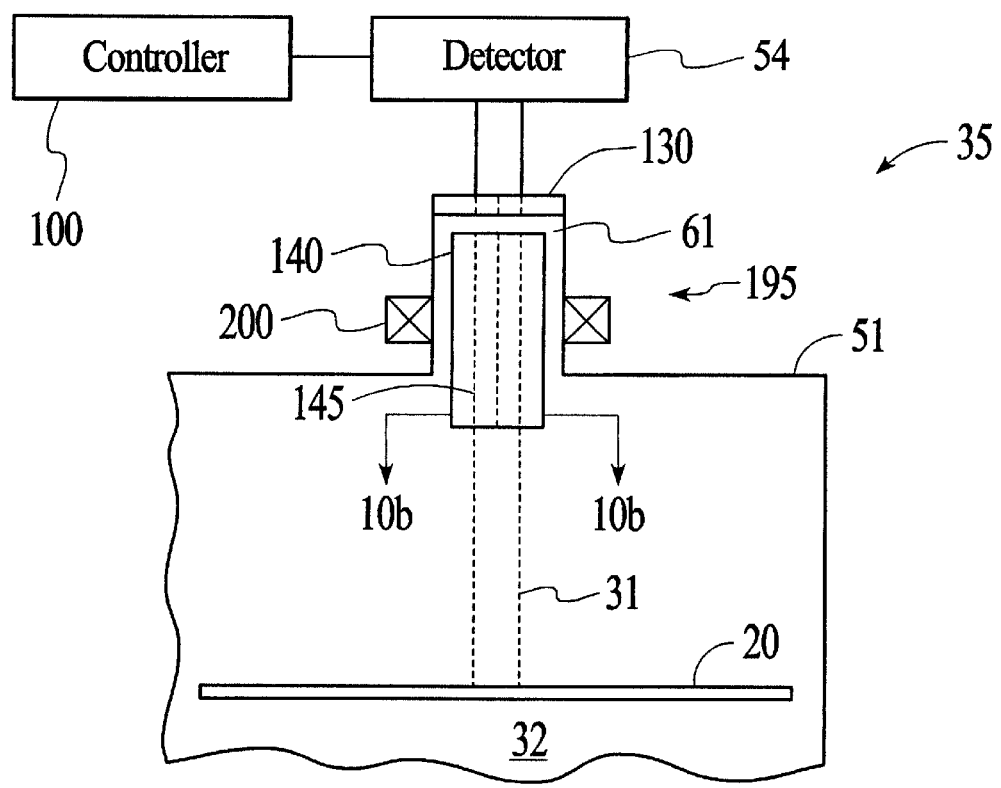
Figure 10B:
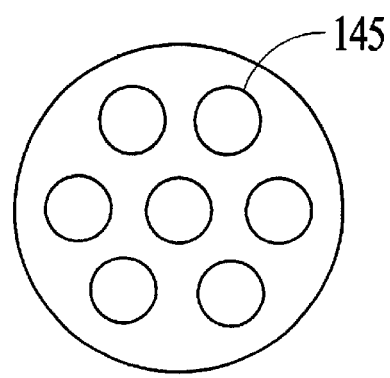
Figure 11:
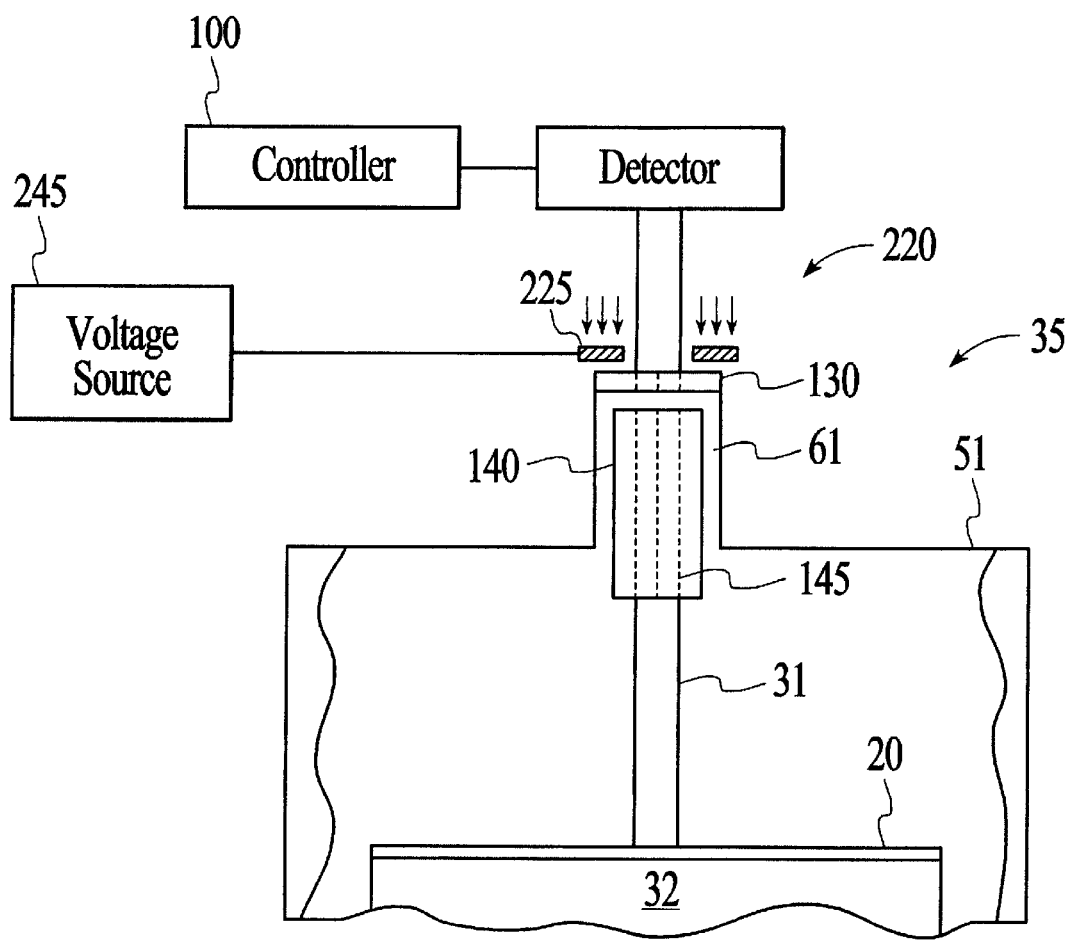
Figure 12:
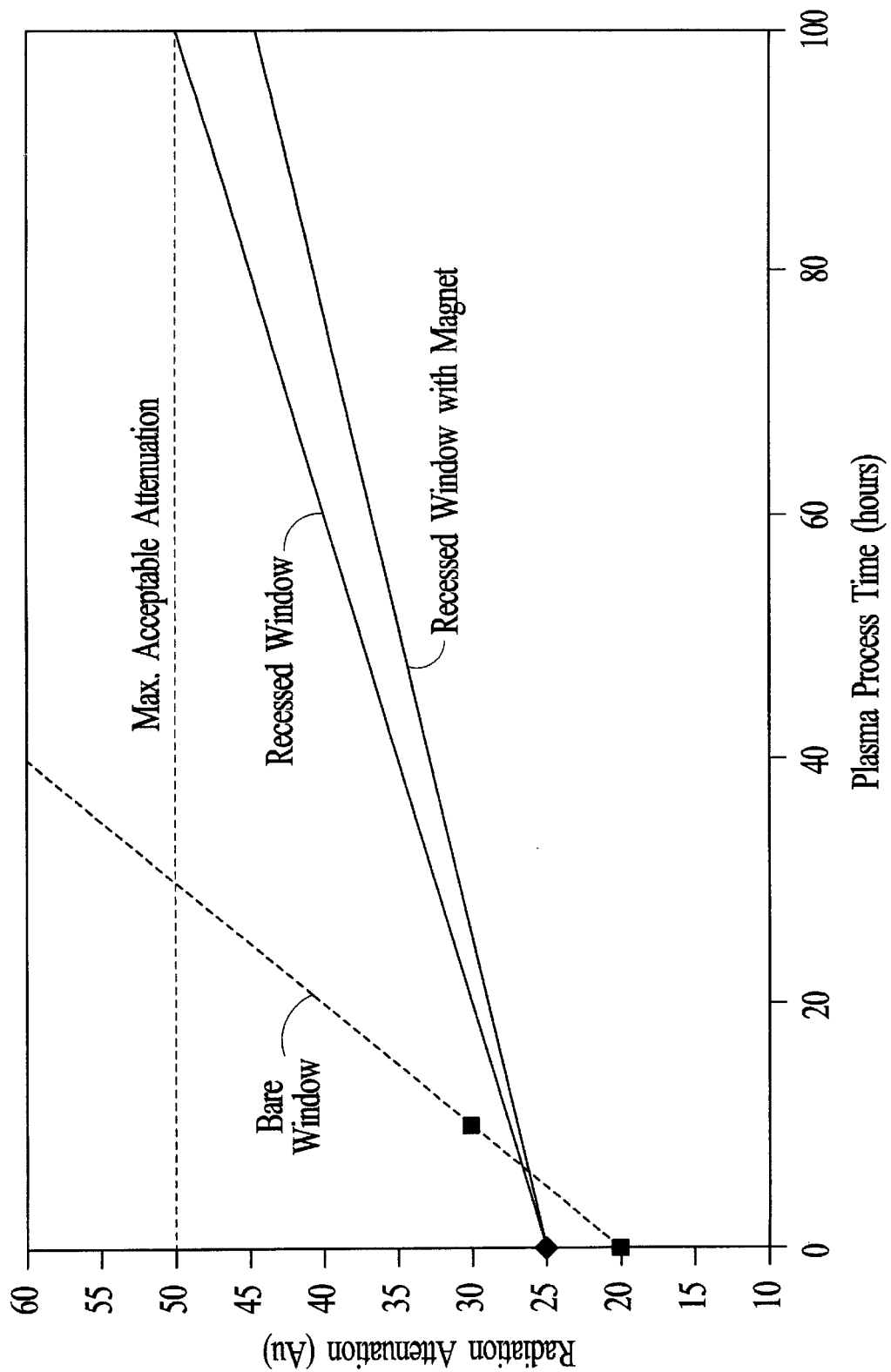
Figure 13:
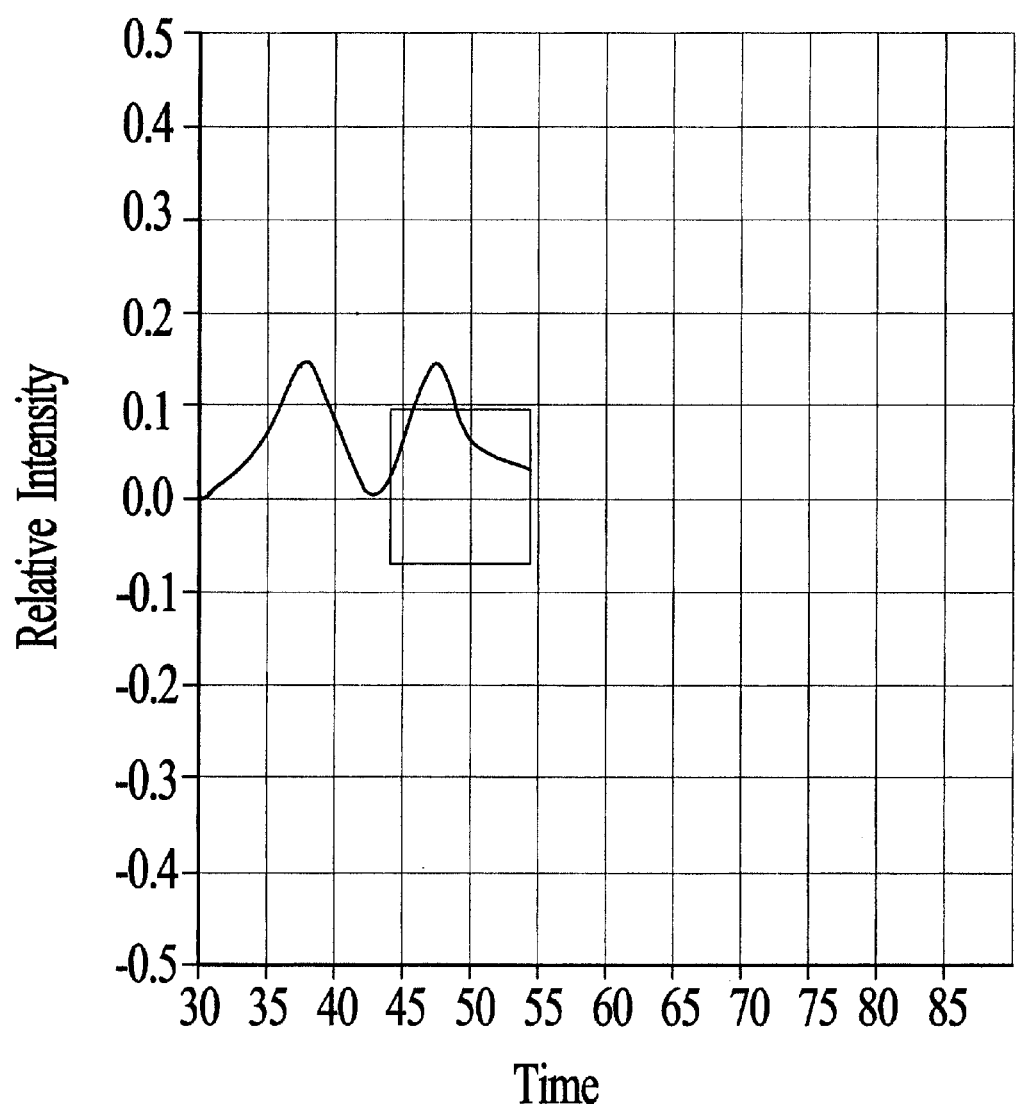

FIGS. 5a and 5b are graphs of partial traces of the amplitude of the reflected radiation tected during the etching of trenches sized 0.4 and 1 micron, respectively, in a silicon dioxide layer ving an open area of 30%;

FIG. 6 is a graph showing the quality of the intensity of the summation signal of reflected radiation as a function of feature size and open area of exposed silicon dioxide;

FIG. 7 is a graph showing the % frequency response versus normalized frequency for multiple passes of the bandpass filter;

FIGS. 8a and 8b are schematic sectional side views of a chamber and process monitoring system according to the present invention;

FIG. 9 is an illustrative block diagram of a computer program suitable for operating the chamber and monitoring a process performed therein;

FIG. 10a is a schematic sectional side partial view of a chamber having a recessed window with a mask and a magnetic field generator positioned to reduce the deposition of process residue on the window;

FIG. 10b is a schematic plan view of the window mask of FIG. 9a;

FIG. 11 is a schematic sectional side partial view of yet another version of a chamber having a recessed window with a mask and an electrical field generator positioned to reduce the deposition of process residue on the window;

FIG. 12 is a graph showing the attenuation of radiation with process time for a bare window, a recessed window with an overlying mask, and a recessed window with an overlying mask and adjacent magnets; and FIG. 13 shows a reflected radiation signal trace after polarization of the radiation, rationing detected polarized radiation signals, and processing the ratioed signal through two cycles in a bandpass filter.

DESCRIPTION

Figure 1A:
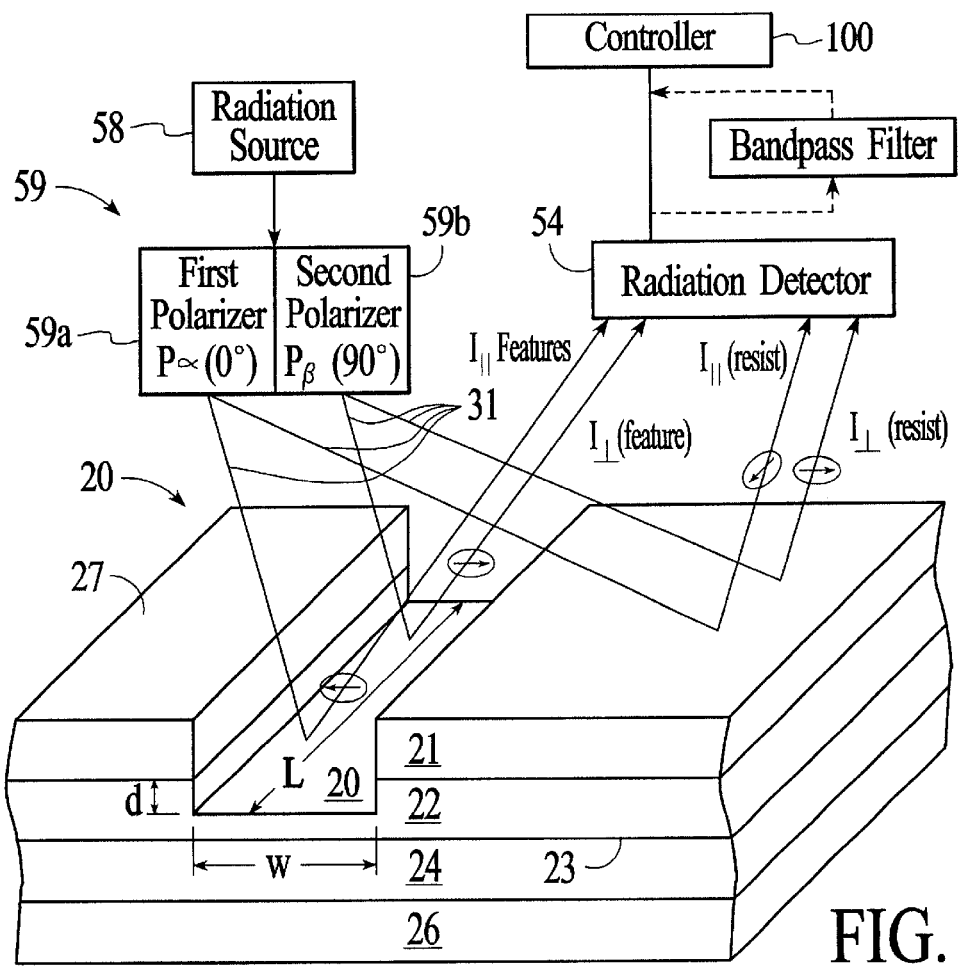
FIG. 1a is a schematic diagram of a first feature being etched in a substrate and an apparatus for receiving substrate reflected radiation having a plurality of polarization angles.
Figure 1B:
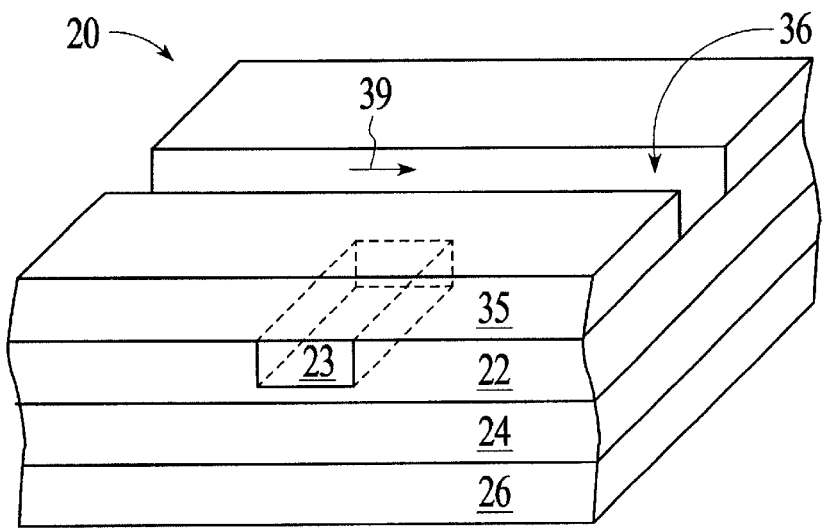
FIG. 1b is a schematic diagram of another feature being etched in the substrate of FIG. 1a, the principal orientation of the second feature being different than the principal orientation of the first feature.

The present invention is useful for monitoring processing of a substrate 20, for example, to detect completion of a stage of processing of a feature 25 being processed on the substrate 20. For example, as illustrated in FIGS. 1a and 1b, the substrate 20 may comprise an etch-resistant material 21 (resist), for example, a photoresist or hard mask layer, that is in a desired patterned configuration. The etch-resistant material 21 overlies other materials 22, 24 which may be shaped as layers and which are formed on a wafer 26 of silicon, compound semiconductor or dielectric. The layers 22, 24 are stratums of the substrate 20 which may be composed of a single material or more than one material. During processing of the materials 22, 24, for example when etching the materials, it may be desirable to stop processing upon approaching or reaching an interface 23 between the first material 22 and the second material 24 or after completion of processing one or both of the first or second materials 22, 24. For example, when etching a feature 25, such as a via or trench in the substrate 20, it may be desirable to stop or slow down the etching process upon reaching a predetermined depth of the first material 22 or after etching through only a small portion of the underlying second material 24. Although an etching process is provided to illustrate an exemplary application of the present invention, it should be understood that the invention may also be applied to materials formed during the deposition of material on the substrate 20 or other processing methods.

The features 25 formed in a particular layer 22 on the substrate 20 may also have an orientation 33, such as a principal orientation, which along a primary direction. For example, the features 25 may be oriented in a principal orientation so that electrical signals may be more expeditiously passed therethrough. In other layers 35, formed above or below the layer 22 being etched, for example, as shown in FIG. 1b, the features 36 may be oriented in other or second principal orientations 39 that are different from the first principal orientation 33 of the features 25 in the first layer 22. For example, the features 36 in the second layer 35 may be mostly oriented in a direction 39 that is perpendicular to the orientation 33, i.e., if the features 25 in the first layer 22 are oriented primarily along a 0° direction, then the features 36 in the overlying second layer 35 may be mostly oriented along a 90° orientation. For example, electrical interconnect lines on adjacent upper and lower levels which are oriented perpendicular to each other reduce problems such as hot spots or excessive inductance-capacitance (LC) crosstalk during operation, especially as the frequency or speed of signal passing through is increased.

In one aspect of the present invention, processing of the substrate 20 is monitored by monitoring an amplitude of the radiation reflected from the substrate, and enhancing the signal strength of the amplitude modulation of radiation reflected from the features 25 relative to the intensity modulation of radiation reflected from the etch-resistant material 21, by detecting substrate reflected radiation 31 having one or more polarization angles. The polarization angle is the mode of vibration of the radiation 31 in the plane perpendicular to the direction of travel of the radiation. For example, FIG. 1a also shows radiation 31 having a plurality of polarization angles being reflected from a feature 25 being etched and from the etch-resistant material 21 on the substrate 20. The radiation 31 is polarized to one or more polarization angles related to an orientation 33, for example, a principally orientation, of a feature 25 being processed on the substrate 20. For example, the radiation 31 may be polarized along polarization angles which are substantially parallel or perpendicular to the principal orientation 33 of the feature 25. The polarization angles may include, for example, a first polarization angle $P_\alpha$ (0°) that is substantially parallel to the principal orientation 33 and a second polarization angle $P_\beta$ (90°) substantially perpendicular to the principal orientation 33.

Referring to FIG. 1a, the intensity of the feature reflected radiation component $I_\parallel$ (or p-component) having a first polarization angle that is substantially parallel to, or directed along the length 1 of, the principal orientation 33 of the feature 25, has a larger magnitude than feature reflected radiation components which are at other polarization angles relative to the principal orientation. For example, the radiation component $I_{195}$ (or s-component) having a polarization angle that is substantially parallel to the width w of the orientation 33 of the feature 25, has a smaller magnitude than reflected radiation at other polarization angles. The measured $I_\parallel$ and $I_{195}$ components may be used to enhance the feature reflected component, from the equations:

$$I_{81\ (sum)} = I_{81\ (feature)} + I_{\parallel(resist)}$$

$$I_{195\ (sum)} = I_{\perp(feature)} + I_{\perp(resist)}$$

The difference or summation of these equations allow separation of the feature reflected component and the etch-resistant material reflected component, as follows:

$$\Delta I = I_{\perp(sum)} - I_{\parallel(sum)} = I^{\perp(feature)} - I_{\parallel(feature)}$$

This occurs because the $I^{\parallel(resist)}$ component is the same as the $I_{\perp(resist)}$ component, and consequently, it cancels out from the equation, leaving behind only the feature reflected components. Thus, monitoring substrate reflected radiation at a plurality of polarization angles can more accurately determine the intensity of the feature reflected components.

Figure 2A:
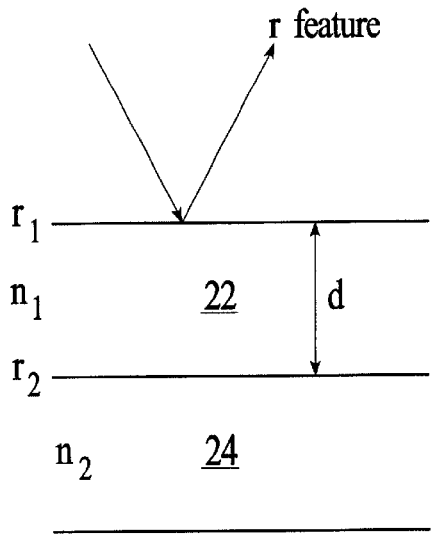
FIGS. 2a and 2b are schematic diagrams showing the constructive and destructive interference effects occurring when radiation is reflected from features being etched in an oxide layer and from the surface of the etch-resistant material, before and after partially etching the features, respectively.
Figure 2B:
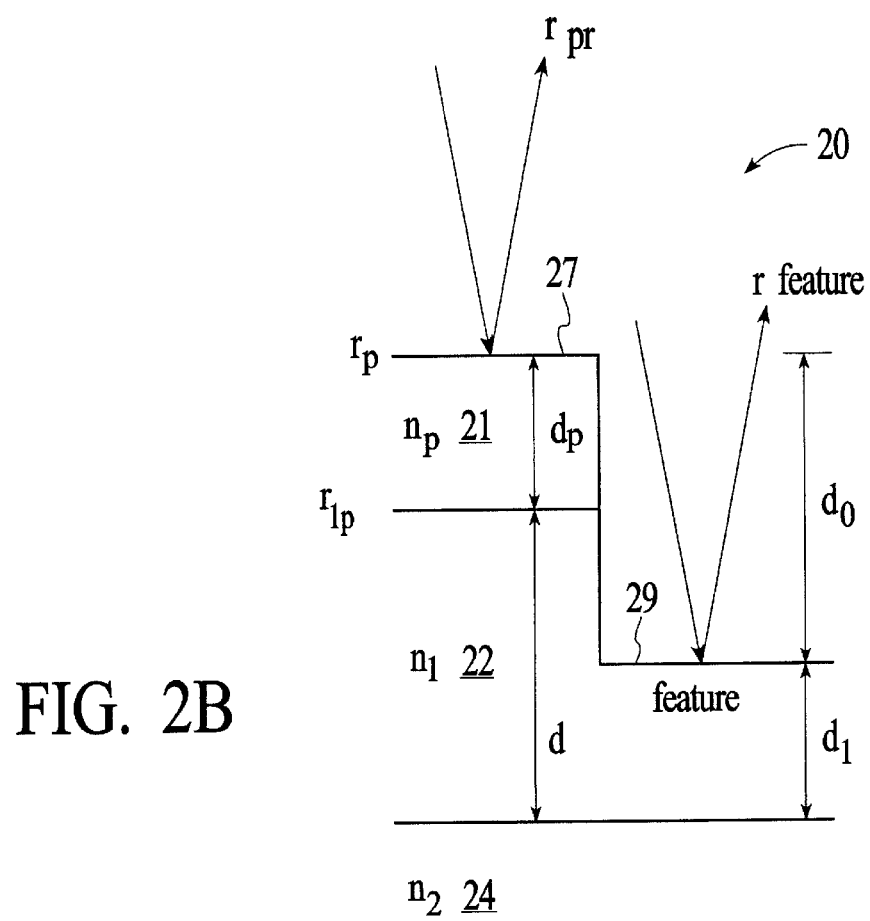

This phenomena may be explained with reference to FIGS. 2a and 2b, which show that the vertical constructive/destructive phase interference may be defined using the ratio of the amplitude of the reflected radiation to the amplitude of the incident radiation, the radiation being for example, light, in the equation $$r_{sum} = (r_1 + r_2 * e^{-i\delta 1})/(1 + r_1 * r_2 * e^{-i\delta 1}),$$

where $$r_1 = (1-n_1)/(1+n_1);\ r_2 = (n_1-n_2)/(n_1+n_2);$$

and $\delta_1 = 4\pi n_1 d_1/\lambda$; and where $n_1$ and $n_2$ are the index of reflection of a feature in an oxide layer and the substrate, respectively, $d_1$ is the thickness of the oxide layer, and $\lambda$ is wavelength. The lateral interference effect is provided by $$I_r = I_0 |f_{pr} r_{pr} + e^{-i\delta} f_{feature} r_{feature}|^2,$$

where $f_{pr}$ is the percentage of photoresist covered area,
$f_{feature}$ is the percentage of feature open area, $$r_{1pr} = (r_{1p} + r_2 * e^{-i\delta 1}))/(1 + r_{1p} * r_2 * e^{-i\delta 1})$$

where $r_{1p} = (n_p - n_1)/(n_p + n_1)$
$r_2 = (n_1 - n_2)/(n_1 + n_2)$, and
$\delta_1 = 4\pi n_1 d_{feature}/\lambda$ $$r_{pr} = (r_p + r_{1pr} * e^{-i\delta 2})/(1 + r_p * r_{1pr} * e^{-i\delta 2}),$$

where $r_p = (1-n_p)/(1+n_p)$, and
$\delta_2 = 4\pi n_p d_p/\lambda$, and $$r_{feature} = (r_1 + r_2 * e^{-i\delta 3})/(1 + r_1 * r_2 * e^{-i\delta 3})$$

where $\delta_3 = 4\pi n_1 d_1/\lambda$, and $\delta_0 = 4\pi d_0/\lambda$.

Figure 3:
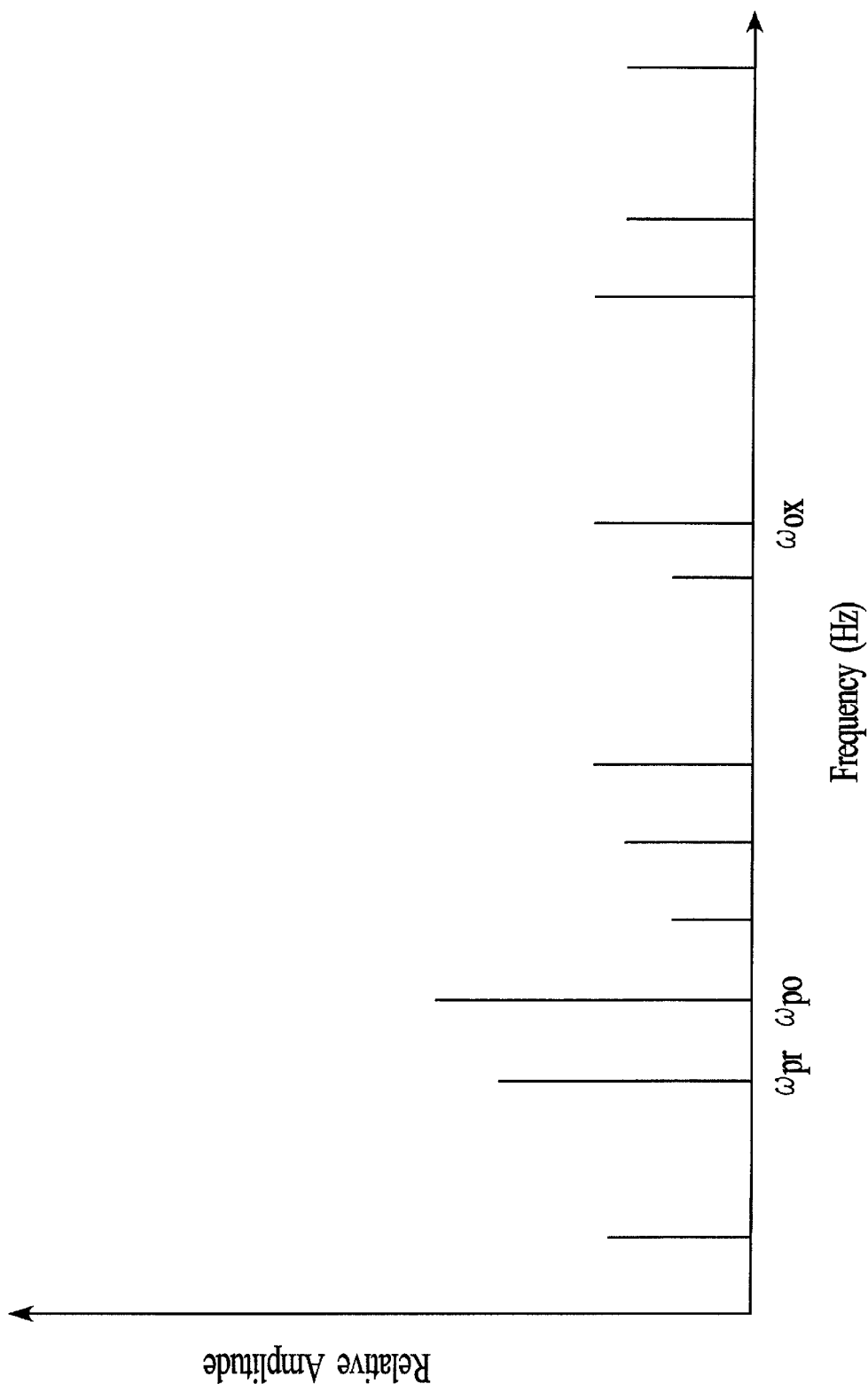
FIG. 3 is a graph of the relative amplitude of different frequencies of the interference signal of the substrate reflected radiation.

The intensity of the radiation reflected from the feature is given by $I_{sum} = I_0 |r_{sum}|^2$. The complex frequency components due to the combination of vertical and lateral interferences are, $w_{pr}$ (photoresist component), $w_{ox}$ (silicon dioxide component), $w_{po}$ (difference between photoresist and silicon dioxide), $w_{ox} - w_{pr}$, $w_{ox} + w_{pr}$, $w_{po} - w_{pr}$, $w_{po} + w_{pr}$, $w_{po} - w_{pr}$, $w_{po} + w_{pr} + w_{ox}$, $w_{ox} - w_{pr} - w_{po}$ and $w_{ox} + w_{pr} - w_{po}$. However, a problem with the change in frequency components as a function of amplitude arises because the shape of interference fringes is distorted due to the coupling of the vertical and lateral interference effects. For example, FIG. 3 shows the relative amplitude and frequencies of the different frequency components $w_{pr}$, $w_{ox}$ and $w_{po}$. Generally, the depth of etching a feature 25 in a substrate 20 is related to the wavelength of the incident radiation by the equation, feature etch depth=wavelength/(2*IOR), where IOR is the index of reflection of the incident radiation. As the etching depth of a feature 25 being processed on a substrate 20 increases, the reflected radiation from the etched features 25 undergoes destructive/constructive interference to provide a detectable oscillating signal having a first frequency that is related to the etching rate and wavelength of the incident radiation. Meanwhile, the radiation reflected from the remaining surface of the substrate 20, which is etched at a different etching rate, also undergoes destructive/constructive interference to provide a detectable oscillating signal having a different and second frequency.

Figure 4A:
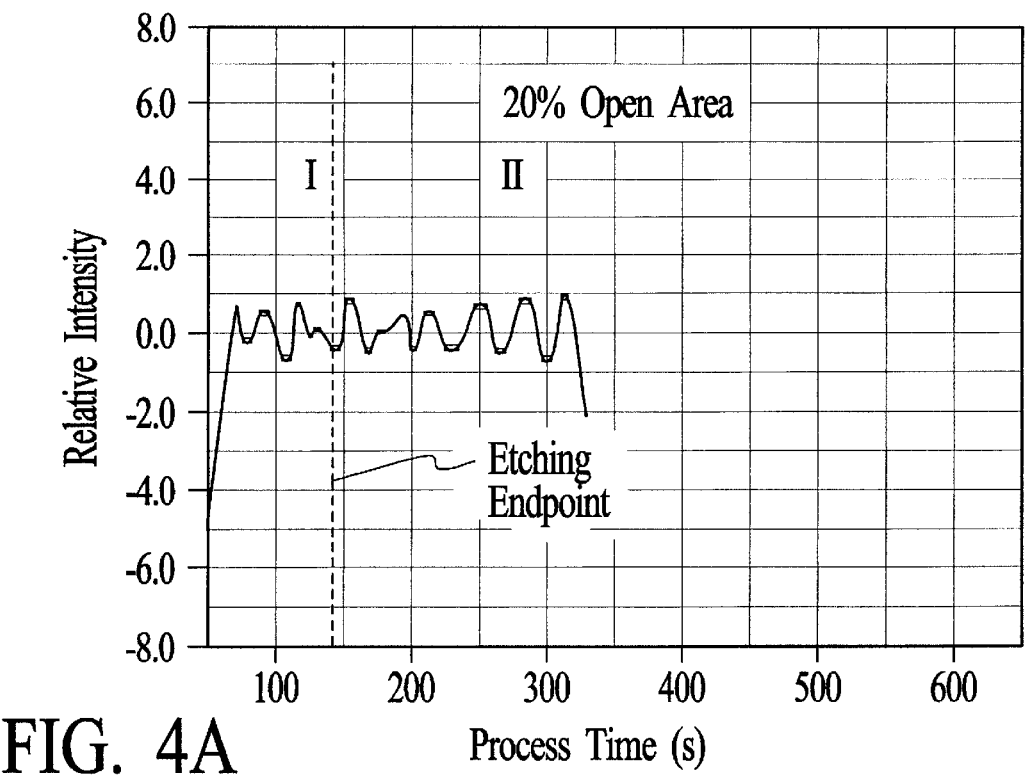
FIGS. 4a and 4b are partial traces of the amplitude of the reflected radiation detected during the etching of 0.4 micron trenches in a silicon dioxide layer having an open area of 5% and 20%, respectively.
Figure 4B:
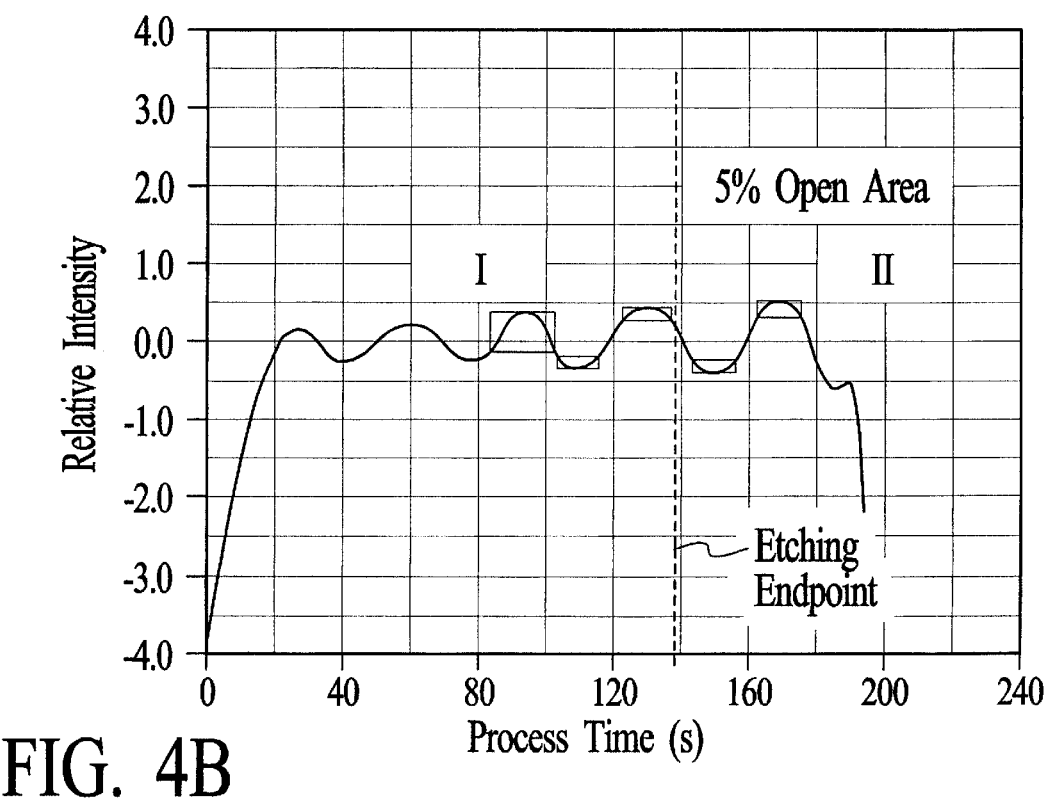

Detection of the modulations of the feature component is especially difficult when the substrate 20 has a small open area between the etch-resistant features 21 because the modulation of the resist component from the larger area of the etch-resistant features 21 dominates the modulation of the total signal. FIG. 4a shows a trace of the reflected radiation signal obtained during the etching of features 25 comprising trenches having openings sized about 0.4 micron in a silicon dioxide dielectric layer on a substrate 20 having an open area of at least about 20%. This trace of the summation signal comprises a first stage (I) in which both the features 25 being etched and the resist material 21 which is also being partially removed, contribute the components which interfere with one another and both contribute to the detected oscillating modulated amplitude that changes unpredictably in frequency and shape. However, the second stage (II) which corresponds to etching of substantially only the etch-resistant material 21 (because the features 25 are fully etched) provides an amplitude trace having a more repeatable cyclic wavefront that is composed of mostly the resist component. The endpoint of the etching process, lying between the two traces and at a cumulative processing time of about 140 seconds, is denoted by "Etching Endpoint". When similar trace studies were conducted for a substrate 20 having a smaller fraction of open area, for example, an open area of 5%, as shown in FIG. 4b, the detected reflected radiation provided a signal trace having a cyclic and repeatable waveform that is mostly the signal intensity of the resist component that is reflected from the surface of the etch-resistant material 21 which occupies more than 95% of the area of the substrate 20. The reflected radiation from the relatively small open area of the features 25 on the substrate 20 that were being etched had a much smaller relative signal intensity that is lost in the larger resist component signal.

It was also determined that the intensity of summation signal is also dependent upon the size of the features 25 being etched in the substrate 20. FIGS. 5a and 5b show amplitude traces obtained during the etching of 0.4 micron and 1 micron features in silicon dioxide on polysilicon over a silicon substrate 20, respectively, both substrates having the same open area of 30%. Again, the first stages, corresponding to etching of both overlying etch-resistant material 21 and the silicon dioxide, provided a summation amplitude trace having complex and variable shape; whereas, the second stages, corresponding to etching of substantially only residual resist, provided a summation amplitude trace having a repeatable and cyclic waveform.

FIG. 6 shows the relationship between the quality of the summation signal in relation to the size of the features 25 being processed or etched in the substrate 20 and as a function of the exposed area of silicon dioxide on the substrate 20. There are two regimes, one in which intensity of summation signal is acceptable, and the other in which the summation signal intensity is not acceptable. The etching feature window 41 denotes a typical region of etched feature size and substrate open area in which many current trench features are processed. Thus, conventional process monitoring methods only allow a small window region of the reflected radiation to be analyzed when the feature size or open area on the substrate becomes small.

In another aspect of the present invention, a filter 53 may be used to selectively filter a signal generated by the radiation detector 54 in relation to a detected intensity of the reflected radiation. In one version, the filter 53 is a bandpass filter that increases the relative intensity of a selected passband of frequencies in relation to the intensity of other frequency components of the reflected radiation. For example, the bandpass filter 53 may be adapted to filter the incoming signal from the radiation detector 54 to pass through a band of frequencies that are related to a frequency of a radiation that is reflected from a feature 25 being processed on the substrate 20, while reducing the intensity of the signal that arises from radiation that is not reflected from the features 25 being processed on the substrate 20. The type of bandpass filter 53 used depends upon the intended process use and the passband frequency limits. In one version, the bandpass filter 53 is an electrical signal processor that operates by filtering the signal and selectively passing thorough only a passband of frequencies. The electrical signal processor may be a digital signal processor that digitizes a radiation signal received from a radiation detector, and filters the digitized signal.

In one version, the selected frequency is approximately the central frequency of the passband. For example, if the bandpass filter has a passband ranging from A to B Hz, the center frequency is (A+B)/2 Hz. When the passband frequency range is centered about a selected frequency of the destructive/constructive interference signals obtained from the radiation component that is reflected from the etched features 25, thereby dampening or excluding the destructive/constructive signal that arises from the radiation component that is reflected from the remaining surface of the substrate 20, for example, a patterned etch-resistant material on the substrate 20. However, the selected frequency does not have to be the center frequency of the passband. That is, comparable results can be achieved by selecting with other frequencies within the passband. In one example, the passband frequency range includes frequencies that are within about +_10% of a selected frequency of a radiation component that is reflected from the substrate 20. For example, for trench shaped features 25 being etched in a dielectric material on a substrate 20, a suitable frequency is from about 0.09 Hz to about 0.11 Hz, for an oxide etch rate of about 5000 angstroms/min.

In one version, the passband frequency range may be selected to provide a coherence length of a non-coherent radiation source 58, which may be, for example, a plasma emission having multiple wavelengths and phases. The coherence length is the length in which interference effects of radiation from the radiation source 58 may be observed. For a non-coherent radiation source, the coherence length is related to the equation $\lambda^2/n\Delta\lambda$, where n is the index of refraction of the layer 22 being etched, $\lambda$ is the wavelength at the center of the plasma emission spectrum, and $\Delta\lambda$ is the wavelength range, and hence the frequency range, passed by the bandpass filter. The coherence length may be obtained when $\Delta\lambda$ is chosen such that $\lambda^2/\Delta\lambda$ is greater than the thickness of the layer 22 being etched. In one version, the $\Delta\lambda$ of the bandpass filter 53 may be 1.5 nanometers for a plasma emission centered about 254 nanometers.

The reflected radiation signal may also be processed in one or more cycles through the bandpass filter 53, so that in each cycle, the signal is filtered to pass through the component of the radiation signal corresponding to the frequencies of reflected radiation from the etched features 25, while dampening the radiation signal corresponding to the frequencies of the reflected radiation from the other or resist 21 portions of the substrate 20. For example, during an etching process, in each pass, the bandpass filter 53 would increase the signal strength of the radiation reflected from the etched features 25 relative to the signal strength of the radiation reflected from the remaining substrate surface. A suitable number of cycles is from about 1 to about 10 cycles, and more typically from about 2 to about 5 cycles.

FIG. 7 shows a graph with the frequency response (%) versus normalized frequency for multiple passes through the bandpass filter 53 showing the increase in strength of radiation having frequencies centered about the etched feature component relative to, for example, the resist component or the rotating magnetic field component that is used during processing. As the number of passes were increased from 1 to 2, the resultant reduction in amplitude of the non-feature reflected radiation component enhanced the signal to noise ratio of the reflected radiation signal from the feature in relation to the other signals from the other surfaces of the substrate.

The present invention is useful for etching a substrate 20 in an apparatus 27, as for example, schematically illustrated in FIG. 8a and FIG. 8b. Generally, the apparatus 27 comprises a chamber 35 having a support 32 for receiving a substrate 20 in a process zone 30. Process gas may be introduced into the chamber 35 through a gas supply 34 comprising a gas source 36, gas inlets 38 located around the periphery of the substrate 20 (as shown) or in a showerhead mounted on the ceiling of the chamber (not shown). A gas flow controller 40 may be used to control the flow rate of the process gas. Spent process gas and etchant byproducts are exhausted from the chamber 35 through a gas exhaust 42 comprising roughing and turbomolecular pumps (not shown) and a throttle valve 44 which may be used to control the pressure of process gas in the chamber 35.

An energized gas or plasma is generated from the process gas by a gas energizer 46 that couples electromagnetic energy to the process gas in the process zone 30 of the chamber 35. For example, a first process electrode 55, such as a sidewall of the chamber 35 and a second electrode 52, such as an electrically conducting portion of the support 32 below the substrate 20 may be used to further energize the gas in the chamber 35, as shown in FIG. 8a. The first and second electrodes 52, 55 are electrically biased relative to one another by an RF voltage provided by an electrode voltage supply 62. The frequency of the RF voltage applied to the electrodes 52, 55 is typically from about 50 KHz to about 60 MHz. As another example, the gas energizer 46 may comprise an inductor coil 47 which inductively couples electromagnetic energy to the gas in the chamber 35, as shown in FIG. 8b.

The radiation 31 incident on the substrate 20 may be provided by a radiation source 58, which may be, for example, a plasma inside or outside the chamber, radiation lamp, LED or laser. The radiation source 58 may provide radiation such as ultraviolet (UV), visible or infrared radiation; or it may provide other types of radiation such as X-rays. The radiation source 58 may comprise, for example, an emission from a plasma generated inside the chamber 28 which is generally multispectral with multiple wavelengths extending across a spectrum, as shown in FIG. 8a, and also generally non-coherent, i.e., with multiple phases. The radiation source 58 may also be positioned outside the chamber 35 so that the radiation 31 may be transmitted from the source 58 through a window 130 and into the chamber 35, as shown in FIG. 8b. The radiation source 58 may also provide radiation having predominant characteristic wavelengths, for example, a single wavelength, such as monochromatic light, as provided by a He-Ne or Nd-YAG laser. The laser source also provides coherent light with a predominant or single phase. Alternatively, the radiation source 58 may comprises a lamp that provides a radiation emission having multiple wavelengths, such as polychromatic light, which may be selectively filtered to a single wavelength. Suitable radiation sources 58 for providing polychromatic light include Hg discharge lamps that generate a polychromatic light spectrum having wavelengths in a range of from about 180 to about 600 nanometers; arc lamps such as xenon or Hg-Xe lamps and tungsten-halogen lamps; and light emitting diodes (LED).

In one version, a non-polarized radiation source 58 that provides a source of non=polarized light, such as ultraviolet, infrared or visible light, is used. The non-polarized source is useful when polarized radiation is preferentially absorbed during the process, by for example, the energized gas or plasma or a residue that accumulates on the chamber window. The polarization state also influences the radiation absorption characteristics in materials having oriented crystalline structures, such as crystals having other than cubic symmetry.

A normal incidence of the radiation onto the substrate 20 may also be used to accurately detect processing endpoints for a substrate 20 having tall and narrowly spaced features, for example, the etch-resistant features, over the layers 22, 24. The normal incident radiation is not blocked from reaching the layers 22, 24 by the height of the etch-resistant material features. However, it should be understood that normal incidence is not necessary for detection of the reflected radiation and that other angles of incidence may be employed.

The radiation may be polarized to a plurality of polarization angles by placing first and second radiation polarizers 59a, 59b in the radiation pathway incident upon and reflected back by the substrate 20. While the present example shows the first and second radiation polarizers 59a, 59b in the pathway of radiation that is incident upon the substrate 20, they can also be in the pathway reflected back by the substrate 20, or they can be part of the radiation detector 54. The first polarizer 59a selectively pass radiation that is oriented at a first polarization angle and the second polarizer 59b selectively passes radiation oriented at a second polarization angle. The first and second polarizers 59a,b may be a single structure or more than one structure. In one version, the polarizers 59a,b comprise radiation permeable material coated with one or more thin films that selectively polarize the radiation passing through the material, or in another version, they may be a rotatable filter. When a rotating polarizer 59a,b is used, the radiation is sampled at periodic intervals to obtain only the reflected radiation signal components that are related to the feature angle orientation.

One or more radiation detectors 54 are used to detect the radiation 31 reflected by the substrate 20. The radiation detectors 54 may comprise a radiation sensor, such as a photovoltaic cell, photodiode, photomultiplier, or phototransistor. The radiation detector 54 provides an electrical output signal in response to a measured intensity of the reflected radiation which may comprise a change in the level of a current passing through an electrical component or a change in a voltage applied across an electrical component. A plurality of radiation detectors 54 may also be used (not shown) with each detector set to capture radiation having a different polarization angle. The detector signals are evaluated to separate the reflected radiation signals from the features 25 and the etch-resistant material 21 reflected radiation components by a controller 100. The controller 100 can also be adapted to evaluate the detected signal to determine the magnitude of radiation having different polarization angles.

The substrate reflected radiation may be detected at a small incident angle or along a substantially vertical direction. The vertical detection angle allows more accurate monitoring of features 25 being processed in the chamber 35, for example, to determine a depth of etching of the features 25 or a depth of material deposited into a feature 25 or as a layer on the substrate 20. The vertical angle is especially desirable when the features 25 being etched have high aspect ratios, and it is difficult for radiation directed at a small incident (or reflected) angle to penetrate the depth of the feature 25 without being blocked by sidewalls of the feature 25 or the sidewalls of the patterned etch-resistant material 21. The vertical detection angle may be obtained by positioning the radiation detector 54, and optionally the radiation source 58 (other than a plasma source which is already above the substrate 20), vertically above the substrate 20.

The chamber 35 may be operated by a controller 100 that executes a computer-readable process control program 102 on a computer system 104 comprising a central processor unit (CPU) 106, such as for example a 68040 microprocessor, commercially available from Synergy Microsystems, California, or a Pentium Processor commercially available from Intel Corporation, Santa Clara, Calif., that is coupled to a memory 108 and peripheral computer components. The memory 108 comprises a computer-readable medium having the computer-readable program 102 embodied therein. Preferably, the memory 108 includes a hard disk drive 110, a floppy disk drive 112, and random access memory 114. The computer system 104 further comprises a plurality of interface cards including, for example, analog and digital input and output boards, interface boards, and motor controller boards. The interface between an operator and the controller 110 can be, for example, via a display 118 and a light pen 120. The light pen 120 detects light emitted by the monitor 118 with a light sensor in the tip of the light pen 120. To select a particular screen or function, the operator touches a designated area of a screen on the monitor 118 and pushes the button on the light pen 120. Typically, the area touched changes color, or a new menu is displayed, confirming communication between the user and the controller 110.

Computer-readable programs such as those stored on other memory including, for example, a floppy disk or other computer program product inserted in a floppy disk drive 112 or other appropriate drive, or stored on the hard drive, may also be used to operate the controller 100. The process control program 102 generally comprises process control software 124 comprising program code to operate the chamber 28 and its components, process monitoring software 126 to monitor the processes being performed in the chamber 28, safety systems software, and other control software. The computer-readable program 102 may be written in any conventional computer-readable programming language, such as for example, assembly language, C$^{++}$, Pascal, or Fortran. Suitable program code is entered into a single file, or multiple files, using a conventional text editor and stored or embodied in computer-usable medium of the memory 108 of the computer system. If the entered code text is in a high level language, the code is compiled, and the resultant compiler code is then linked with an object code of pre-compiled library routines. To execute the linked, compiled object code, the user invokes the object code, causing the CPU 106 to read and execute the code to perform the tasks identified in the program.

FIG. 9 is an illustrative block diagram of a hierarchical control structure of a specific embodiment of a process control program 102 according to the present invention. Using a light pen interface, a user enters a process set and chamber number into a process selector program 132 in response to menus or screens displayed on the CRT terminal. The process chamber program 124 includes program code to set the timing, gas composition, gas flow rates, chamber pressure, RF power levels, support position and other parameters of a particular process. The process sets are predetermined groups of process parameters necessary to carry out specified processes. The process parameters are process conditions, including without limitations, gas composition, gas flow rates, pressure, and gas energizer settings. In addition, parameters needed to operate the process monitoring program 126 are also inputted by a user into the process selector program. These parameters include known properties of the materials being processed, especially radiation absorption and reflection properties, such as reflectance and extinction coefficients; process monitoring algorithms that are modeled from empirically determined data; tables of empirically determined or calculated values that may be used to monitor the process; and properties of materials being processed on the substrate.

The process sequencer program 134 comprises program code to accept a chamber type and set of process parameters from the process selector program 132 and to control its operation. The sequencer program 134 initiates execution of the process set by passing the particular process parameters to a chamber manager program 136 that controls multiple processing tasks in the process chamber 28. Typically, the process chamber program 124 includes a substrate positioning program 138, a gas flow control program 140, a gas pressure control program 142, a gas energizer control program 144 and a heater control program 146. Typically, the substrate positioning program 138 comprises program code for controlling chamber components that are used to load the substrate 20 onto the support 32 and optionally, to lift the substrate 20 to a desired height in the chamber 35 to control the spacing between the substrate 20 and the gas inlets 38 of the gas delivery system 34 the process gas control program 140 has program code for controlling the flow rates of different constituents of the process gas. The process gas control program 140 controls the open/close position of the safety shut-off valves, and also ramps up/down the gas flow controller 40 to obtain the desired gas flow rate. The pressure control program 142 comprises program code for controlling the pressure in the chamber 28 by regulating the aperture size of the throttle valve 44 in the gas exhaust 42 of the chamber. The gas energizer control program 144 comprises program code for setting low and high-frequency RF power levels applied to the process electrodes 52, 55 in the chamber 35. Optionally, the heater control program 146 comprises program code for controlling the temperature of a heater element (not shown) used to resistively heat the support 32 and substrate 20.

The process monitoring program 126 may comprise program code to obtain sample or reference signals from the radiation source 58, radiation detector 54, or controller 100 and processes the signal according to preprogrammed criteria. Typically, a radiation amplitude or spectrum trace is provided to the controller 100 by an analog to digital converter board in the radiation detector 54. The process monitoring program 126 may also send instructions to the controller 100 to operate components such as the radiation source 58, radiation detector 54 and other components. The program may also send instructions to the chamber manager program 136 or other programs to change the process conditions or other chamber settings.

The process monitoring program 126 may also comprise program code to obtain and evaluate signals from the radiation detector 54. The program code may be designed to reduce the intensity of undesirable frequency components of the reflected radiation, for example, the frequency components that arise from radiation that is not reflected from the features 25 being processed on the substrate 20. For example, the bandpass filter may be adapted to filter an incoming radiation signal from the detector 54 to obtain a frequency band centered about one or more selected frequencies of the radiation reflected from the substrate 20.

To define the parameters of the process monitoring program 126, initially, one or more substrates 20 having predetermined thicknesses of material are selected for processing. Each substrate 20 is placed at one time into the process chamber 35 and process conditions are set to process a material 22 or an underlying material 24 on the substrate 20. Radiation reflected from the substrate and/or emitted from the plasma in the chamber are monitored using one or more radiation detectors 54. After a series of such traces are developed, they are examined to identify a recognizable change in a property of the trace, which is used as input for the computer program, in the form of an algorithm, a table of values, or other criteria for suitable for evaluating an event in the chamber 35 or a property of the substrate 20. For example, the process monitoring program 126 may include program code to evaluate a signal corresponding to an intensity of reflected radiation which may be used to detect both an onset and completion of processing of the substrate 20. As another example, the computer program 126 comprises program code to evaluate first and second signals that correspond to radiation emitted from the plasma and/or reflected from the substrate 20.

Thus, the process monitoring program 126 may comprise program code to analyze an incoming signal trace provided by the radiation detector 54 and determine a process endpoint or completion of a process stage when a desired set of criteria is reached, such as when an attribute of the detected signal is substantially similar to a pre-programmed value. The process monitoring program 126 may also be used to detect a property of a material being processed on the substrate such as a thickness, or other properties, for example, the crystalline nature, microstructure, porosity, electrical, chemical and compositional characteristics of the material on the substrate 20. The computer program 126 may also be programmed to detect both an onset and completion of processing of the substrate 20, for example, by detecting a change in amplitude or a rate of change of amplitude of the radiation 31. The desired criteria are programmed into process monitoring program 126 as preset or stored parameters and algorithms. The program 126 may also include program code for modeling a trace of radiation, selecting a feature from the modeled trace or allowing a user to select the feature, storing the modeled trace or the feature, detecting a portion of an incoming signal from a radiation detector 54, evaluating the measured signal relative to the stored trace or feature, and calling an end of a process stage of the process being performed on the substrate 20 or displaying a measured property of a material on the substrate 20.

In one version, the process monitoring software comprises program code for continuously analyzing a trace of a measured amplitude of reflected radiation by drawing a box or "window" around the end portion of the trace and back in time, with signal height and time length established in the preprogrammed algorithm. A set of windows may be programmed to detect a valley or peak in the trace of the reflected intensity, trigger on an upward slope to detect a later endpoint, or to trigger on a downward slope to detect an endpoint before a valley in the trace. The first criterion is met when the signal in the trace becomes too steep and exits or moves out of the preprogrammed box ("WINDOW OUT") or when Sit becomes gradual and enters the box ("WINDOW IN"). Additional windows are sequentially applied on the moving trace to generate the complete set of criteria to make a determination on whether the change in signal measured in the real time trace is an endpoint of the process, such as an onset or completion of the process, a change in the property of the material, or is only noise. The direction of entering or exiting a box may also be specified as part of the preprogrammed input criteria for operating the process monitoring program 126. Upon detecting an onset or completion of a process, the process monitoring program signals the process chamber program 126 which sends instructions to the controller 100 to change a process condition in a chamber 35 in which the substrate 20 is being processed. The controller 100 is adapted to control one or more of the gas supply 34, gas energizer 46, or throttle valve 44 to change a process condition in the chamber 35 in relation to the received signal.

The data signals received by and/or evaluated by the controller 100 may be sent to a factory automation host computer 300. The factory automation host computer 300 may comprise a host software program 302 that evaluates data from several systems 27, platforms or chambers 35, and for batches of substrates 20 or over an extended period of time, to identify statistical process control parameters of (i) the processes conducted on the substrates 20, (ii) a property that may vary in a statistical relationship across a single substrate 20, or (iii) a property that may vary in a statistical relationship across a batch of substrates 20. The host software program 302 may also use the data for ongoing in-situ process evaluations or for the control of other process parameters. A suitable host software program comprises a WORKSTREAM™ software program available from aforementioned Applied Materials. The factory automation host computer 300 may be further adapted to provide instruction signals to (i) remove particular substrates 20 from the processing sequence, for example, if a substrate property is inadequate or does not fall within a statistically determined range of values, or if a process parameter deviates from an acceptable range; (ii) end processing in a particular chamber 35, or (iii) adjust process conditions upon a determination of an unsuitable property of the substrate 20 or process parameter. The factory automation host computer 300 may also provide the instruction signal at the beginning or end of processing of the substrate 20 in response to evaluation of the data by the host software program 302.

It was further discovered that the signal to noise ratio of the reflected radiation signal could be further improved by placing a window 130 through which the radiation detector 54 views radiation reflected off the substrate in a recess 61 in the wall of the chamber 35. FIG. 10a is a schematic sectional side view of a chamber having a window 130 in a recess in the wall 51 of the chamber 35, a detector 54 to detect the radiation reflected from the substrate and passing through the window 130 and generate a signal in response to the detected radiation, and a controller 100 to evaluate the detected signal to monitor the process. The window 130 comprises a material that is permeable to the wavelengths of radiation that are monitored by the controller 100. For infrared, visible, and UV radiation, the window 130 may be made of a ceramic, such as for example, one or more of $Al_2O_3$, Si, $SiO_2$, $TiO_2$, $ZrO_2$ or mixtures and compounds thereof. The ceramic may also comprise a monocrystalline material, such as for example, sapphire which is monocrystalline alumina and that exhibits good erosion resistance to halogen plasmas, especially fluorine containing plasmas.

The recess 61 in the wall 51 of the chamber 35 is shaped and sized to receive a mask 140 therein, as shown in FIG. 10. For example, when the mask 140 is cylindrical in shape, the recess 61 may also be cylindrically shaped. The mask 140 is sized to substantially cover the window 130 thereby reducing or preventing the deposition of process residues on the window 130. The mask 140 may be made of a material that is resistant to erosion by the process gas or plasma in the chamber 35, such as a plasma resistant material, for example, one or more of $Al_2O_3$, $SiO_2$, AlN, BN, Si, SiC, $Si_3N_4$, $TiO_2$, $ZrO_2$, or mixtures and compounds thereof.

The mask 140 comprises one or more apertures 145 therein, as shown in FIG. 10b. The apertures 145 are shaped and sized to reduce the deposition of process residues therein while allowing a sufficient amount of radiation to pass therethrough to operate the controller 100. For example, the apertures 145 may be shaped and sized to pass both incident and reflected radiation beams therethrough—for interferometric or ellipsometric analysis—or it may be shaped and sized to monitor a spectral emission from the plasma for plasma emission analysis. It is believed that the apertures 145 reduces the deposition of process residues therein by reducing the access of neutral gaseous species (which are often the residue forming species) or by allowing highly energized gaseous ions to etch away process residues that form on the walls of the apertures 145. The aspect ratio and depth of the recess 145 generally control the distance that must be traveled by the energetic gaseous species before they reach the internal surfaces of the recess 145 for example, a window 130 in the recess 145. Suitable apertures 145 comprises an aspect ratio of at least about 0.25:1 and the aspect ratio may also be less than about 12:1. In one version, the apertures 145 comprises an opening size of from about 0.1 to about 50 mm and a depth of from about 0.5 to about 500 mm. The mask 140 may also comprise a plurality of apertures 145, such as for example, a plurality of hexagonal or circular shaped holes.

An electromagnetic field source may be adapted to maintain an electromagnetic field about the window 130. The electromagnetic field source comprises an electrical or magnetic field source. The electromagnetic field applied about the wall 51 may reduce the deposition of process residues on the window 130 in the recess 61 in the wall. For example, in the embodiment shown in FIG. 10a, the electromagnetic field source comprises a magnetic field source 195 adapted to maintain a magnetic field near the portion of the wall 51, about the recess 61, or across the window 130. The magnetic field source 195 comprises at least one magnet 200 or electromagnet (not shown) that is positioned adjacent or abutting the recess, wall or window 130 to provide magnetic energy thereabout. For example, in one version, the magnetic energy may be confined to the space around the recess 61 or window 130 and may penetrate only a small distance into the chamber 35. In this version, the magnetic field source 195 provides a magnetic field that is preferentially concentrated across the recess 61 or window 130 relative to other portions of the chamber 35. Generally, a suitable magnetic field strength may be from about 10 to about 10,000 Gauss, and more preferably from about 50 to about 2000 Gauss, but the actual magnetic strength selected would depend upon the window size, energy of the plasma ions, and other factors. In the embodiment illustrated in FIG. 10a, the magnetic field source 195 comprises a plurality of magnetic poles 200 disposed about a perimeter of the recess in the wall and having opposing magnetic polarities In another embodiment, as illustrated in FIG. 11, the electromagnetic field source comprises an electrical field source 220 that provides electrical energy about the wall 51, recess 61 or across the window 130 (as shown) to maintain an electrical field thereabout. It is believed that the electrical field reduces the deposition of process residues on the wall 51, in the recess 61, or on the window 130, for example, by repelling the charged residue forming species or by causing the energized gaseous species to bombard the window 130 to etch away the process residues. The electric field source 220 may comprise an electrode 225 that is adjacent to, abutting, or behind the wall 51, about the recess 61, or near the window 130, to couple electrical energy thereabout. The electrical field may be adapted to have electrical field components which are parallel or perpendicular to the plane of the wall 51 or window 130. The electrode 225 may be sized sufficiently large to provide an electric field that covers an entire area of the wall 51 or the window 130. The electrode 225 may also comprise eddy current reducing slots that are shaped and sized to reduce any eddy currents that may be induced in the electrode 225. A voltage source 245 electrically biases the electrode 225 with a DC, AC or RF voltage, typically of from about 10 to about 10,000 volts, and more preferably from about 20 to about 4000 volts. 35 FIG. 12 shows the attenuation of radiation over processing time for a bare window, a recessed window 130, and a recessed window 130 with an adjacent magnet 200. It can be seen that radiation passing through a bare, unrecessed window lacking an electromagnetic field source reaches the maximum acceptable attenuation at less than 40 plasma process hours. In comparison, radiation passing through a recessed window 130 reaches the maximum acceptable attenuation in around 100 hours and the radiation passing through a recessed window 130 comprising an adjacent magnet 200 reaches a maximum acceptable attenuation after 100 hours. This data shows that a recessed window 130 provides a substantial reduction in the attenuation of the radiation intensity during a plasma process. Adding an electromagnetic field source, in this case an adjacent magnet 200, substantially enhances this reduction in attenuation.

EXAMPLE

The following example demonstrates the effectiveness of the present invention. However, the present invention may be used in other processes and for other uses as would be apparent to those of ordinary skill in the art and the invention should not be limited to the examples provided herein. In this example, features 25 were etched in a substrate 20 in a magnetically enhanced etching chamber with a recessed window covered by a mask and having a magnetic field generator about the window, as for example illustrated in FIG. 10a. The substrate 20 being etched was a silicon wafer comprising a dielectric layer 22 comprising a 1 micron silicon dioxide layer, a 0.1 micron silicon nitride layer, and a 1 micron silicon dioxide layer. An overlying patterned photoresist layer 21 covered the dielectric layer 22. The dielectric layer 22 was etched using a process gas comprising 40 sccm $CHF_3$, 20 sccm $CF_4$, and 50 sccm Ar. The pressure in the chamber was maintained at 200 mTorr, the process electrode R.F. bias power level at 1300 watts, and portions of the chamber were maintained at temperatures of about 15° C. The etched features 25 had openings sized from about 0.4 micron to about 1 micron, the exposed dielectric (silicon dioxide) area on the silicon wafer was from about 5% to about 50%.

In this example, the radiation reflected from the substrate 20 was detected in two polarization angles, and a bandpass filter was used to evaluate the signal generated from the radiation detector. The first and second radiation detectors were used to detect and measure the p-component and s-component of the polarized radiation. The radiation incident upon the substrate 20 comprised radiation having a wavelength of 254 nm. A passband filter placed in the radiation path was adapted to selectively pass thorough radiation having frequencies within a passband range that was centered about the radiation frequency reflected from the features 25 being etched in the substrate 20.

FIG. 13 shows a signal trace obtained after polarization of the radiation, rationing the detected polarized radiation signals, and processing the ratioed signal through two cycles in a bandpass filter. The incident radiation had a wavelength of 254 nm. The ratio of the radiation reflected from the features 25 and the etch-resistant material 21 and was determined. The ratioed signal trace was processed through two cycles of a bandpass filter. For a substrate having an open oxide area of 50%, the predicted etch depth was identical to the measured etch depth, both at about 0.46 micron. When the same tests were conducted on a substrate having an open oxide area of 30%, the predicted etch depth at 0.49 micron was slightly different from the measured etch depth was 0.5 micron; and for an open oxide area of 20%, the predicted etch depth was 0.46 micron for a measured etch depth of 0.48 micron. These results demonstrate the accuracy of the present method and apparatus.

The present invention is described with reference to certain preferred versions thereof, however, other versions are possible. For example, the endpoint detection process can be used for detecting endpoints in other processes and in other chambers as would be apparent to one of ordinary skill, including without limitation, other types of etching chambers, including but not limited to, capacitively coupled chambers, ion implantation chambers, and deposition chambers such as PVD or CVD chambers. Therefore, the spirit and scope of the appended claims should not be limited to the description of the preferred versions contained herein.

What is claimed is:

1. A substrate processing apparatus comprising:
    a chamber capable of processing a substrate;
    a radiation source to provide a radiation;
    a radiation polarizer adapted to polarize the radiation to one or more polarization angles that are selected in relation to an orientation of a feature being processed on the substrate;

a radiation detector to detect radiation reflected from the substrate during processing and generate a signal; and a controller to process the signal.

2. An apparatus according to claim 1 wherein the radiation is polarized to a plurality of polarization angles.

3. An apparatus according to claim 1 wherein the radiation is polarized to a polarization angle that is substantially parallel, or substantially perpendicular, to the orientation of the feature.

4. An apparatus according to claim 1 wherein the feature comprises a principal orientation, and wherein the radiation is polarized to a first polarization angle substantially parallel to the principal orientation and a second polarization angle substantially perpendicular to the principal orientation.

5. An apparatus according to claim 1 wherein the controller processes the signal to increase the intensity of a signal component arising from the radiation reflected by the feature being processed in the substrate relative to other signal components.

6. An apparatus according to claim 1 wherein the controller processes signal components of reflected radiation that are polarized at different polarization angles.

7. An apparatus according to claim 6 wherein the controller determines a ratio or subtraction product of the reflected radiation signal components.

8. An apparatus according to claim 7 wherein the reflected radiation signal components comprise signal components arising from radiation polarized at polarization angles which are substantially parallel, or substantially perpendicular, to the orientation of the feature.

9. An apparatus according to claim 1 wherein the radiation polarizer comprises one or more polarizing filters.

10. An apparatus according to claim 1 wherein the controller comprises a bandpass filter.

11. An apparatus according to claim 10 wherein the bandpass filter increases the intensity of a signal component arising from the radiation reflected by the feature being processed in the substrate relative to other signal components.

12. An apparatus according to claim 10 wherein the bandpass filter selectively passes through signal frequencies within a frequency passband that is selected in relation to a intensity modulation frequency of radiation reflected from the feature being processed on the substrate.

13. An apparatus according to claim 12 wherein the frequency passband is centered about the modulation frequency.

14. An apparatus according to claim 1 wherein:

the chamber comprises a substrate support, gas supply, gas energizer, and gas exhaust; and the controller analyzes the signal to detect an attribute in the signal related to a process endpoint, the attribute comprising a valley, peak, upward slope or downward slope, in the signal; and the controller operates one or more of the substrate support, gas supply, gas energizer, and gas exhaust, to change a process condition upon detection of the signal attribute.

15. A method of processing a substrate in a process zone, the method comprising the steps of:

(a) providing a substrate in the process zone;

(b) setting process conditions to process the substrate with an energized gas;

(c) providing radiation that is polarized at one or more polarization angles that are selected in relation to an orientation of a feature being processed on the substrate;

(d) detecting radiation reflected from the substrate and generating a signal in response to the detected radiation; and (e) processing the signal.

16. A method according to claim 15 wherein in (c) the radiation is polarized at a plurality of polarization angles.

17. A method according to claim 15 wherein in (c) the one or more polarization angles comprise a polarization angle is substantially parallel, or substantially perpendicular, to the orientation of the feature.

18. A method according to claim 15 wherein in (c) the one or more polarization angles comprise a first polarization angle substantially parallel to the feature orientation and a second polarization angle substantially perpendicular to the feature orientation.

19. A method according to claim 15 wherein the feature is a trench having a principal orientation, and wherein in (c) the one or more polarization angles comprise a polarization angle is related to the principal orientation of the trench.

20. A method according to claim 19 wherein (e) comprises determining a depth of the trench.

21. A method according to claim 15 wherein (e) comprises increasing the intensity of a signal component that arises from the radiation reflected by a feature being processed in the substrate relative to other signal components.

22. A method according to claim 21 comprising processing signal components of reflected radiation that are polarized at different polarization angles.

23. A method according to claim 22 comprising determining a ratio or subtraction product of the reflected radiation signal components.

24. A method according to claim 22 wherein the reflected radiation signal components comprises signal components arising from radiation polarized at polarization angles which are substantially parallel, or substantially perpendicular, to the orientation of the feature.

25. A method according to claim 15 wherein (c) comprises increasing the intensity of a signal component arising from the radiation reflected by the feature being processed in the substrate relative to other signal components.

26. A method according to claim 25 wherein (c) comprising filtering the signal to selectively pass through a frequency passband relating to an intensity modulation frequency of the radiation reflected from the feature being processed on the substrate.

27. A method according to claim 26 wherein the frequency passband is centered about the modulation frequency.

28. A method according to claim 15 wherein (e) comprises analyzing the signal to detect an attribute in the signal related to a process endpoint, the attribute comprising a valley, peak, upward slope, or downward slope, in the signal, and wherein the method further comprises:

changing a process condition upon detection of the signal attribute.

29. A substrate processing apparatus comprising:

a chamber capable of processing a substrate;

a radiation source to provide a radiation;

a radiation polarizer adapted to polarize the radiation to a plurality of polarization angles;

a radiation detector to detect radiation reflected from the substrate during processing and generate a signal; and a controller to process the signal.

30. An apparatus according to claim 29 wherein the plurality of polarization angles are selected in relation to a principal orientation of a feature being processed on the substrate.

31. An apparatus according to claim 30 wherein the plurality of polarization angles are substantially parallel or substantially perpendicular to the principal orientation.

32. An apparatus according to claim 29 wherein the controller processes signal components of reflected radiation that are polarized at the plurality of polarization angles.

33. An apparatus according to claim 32 wherein the controller determines a ratio or subtraction product of the reflected radiation signal components.

34. An apparatus according to claim 29 wherein the controller comprises a bandpass filter to selectively passes through signal frequencies within a frequency passband that is selected in relation to an intensity modulation frequency of radiation reflected from a feature being processed on the substrate.

35. An apparatus according to claim 34 wherein the frequency passband is centered about the modulation frequency.

36. A method of processing a substrate in a process zone, the method comprising the steps of:
   (a) providing a substrate in the process zone;
   (b) setting process conditions to process a feature on the substrate with an energized gas;
   (c) providing radiation that is polarized to a plurality of polarization angles;
   (d) detecting radiation reflected from the substrate and generating a signal in response to the detected radiation; and
   (e) processing the signal.

37. A method according to claim 36 wherein in (c) the plurality of polarization angles are selected in relation to an orientation of a feature being processed on the substrate.

38. A method according to claim 37 wherein the plurality of polarization angles comprise a polarization angle that is substantially parallel, or substantially perpendicular, to the feature orientation.

39. A method according to claim 37 wherein plurality of polarization angles comprise a first polarization angle substantially parallel to the feature orientation and a second polarization angle substantially perpendicular to the feature orientation.

40. A method according to claim 36 wherein (e) comprises increasing the intensity of a signal component that arises from the radiation reflected by a feature being processed in the substrate relative to other signal components.

41. A method according to claim 40 comprising processing signal components of the reflected radiation that are polarized to different polarization angles.

42. A method according to claim 41 comprising determining a ratio or subtraction product of the reflected radiation signal components.

43. A method according to claim 42 wherein the reflected radiation signal components comprise signal components arising from radiation polarized at polarization angles which are substantially parallel, or substantially perpendicular, to the orientation of the feature.

44. A method according to claim 36 wherein (e) comprises filtering the signal to selectively pass through a frequency passband relating to an intensity modulation frequency of the radiation reflected from a feature being processed on the substrate.

45. A method according to claim 44 wherein the frequency passband is centered about the modulation frequency.

46. A substrate processing apparatus comprising:
   a chamber capable of processing a substrate;
   a radiation source to provide a radiation;
   a radiation detector to detect radiation reflected from the substrate during processing and generate a signal; and
   a bandpass filter to filter the signal.

47. An apparatus according to claim 46 wherein the bandpass filter is adapted to selectively pass through frequencies in a frequency passband while reducing the intensity of other frequencies.

48. An apparatus according to claim 46 wherein the bandpass filter increases the intensity of a signal component arising from the radiation reflected by a feature being processed on the substrate relative to other signal components.

49. An apparatus according to claim 46 wherein the bandpass filter selectively passes through signal frequencies within a frequency passband that is selected in relation to an intensity modulation frequency of radiation reflected from the feature being processed on the substrate.

50. An apparatus according to claim 49 wherein the frequency passband is centered about the modulation frequency.

51. An apparatus according to claim 46 wherein the frequency passband comprises a range of about ±10% of the modulation frequency.

52. An apparatus according to claim 46 wherein the bandpass filter comprises an electrical signal processor.

53. An apparatus according to claim 52 wherein the electrical signal processor comprises a digital signal processor.

54. An apparatus according to claim 46 comprising a radiation polarizer adapted to polarize the radiation to a plurality of polarization angles.

55. An apparatus according to claim 54 wherein the radiation polarizer comprises one or more polarizing filters.

56. An apparatus according to claim 46 comprising a radiation polarizer to polarize the radiation to a polarization angle that is related to an orientation of a feature being processed on the substrate.

57. An apparatus according to claim 56 comprising a radiation polarizer adapted to polarize the radiation to a polarization angle that is substantially parallel, or substantially perpendicular, to the orientation of the feature.

58. An apparatus according to claim 56 wherein the feature comprises a principal orientation, and wherein the radiation is polarized to a first polarization angle substantially parallel to the principal orientation and a second polarization angle substantially perpendicular to the principal orientation.

59. An apparatus according to claim 46 comprising a controller adapted to process the signal to increase the intensity of a signal component arising from the radiation reflected by the feature being processed on the substrate relative to other signal components.

60. An apparatus according to claim 59 wherein the controller processes signal components of reflected radiation that are polarized at different polarization angles.

61. An apparatus according to claim 59 wherein the controller determines a ratio or subtraction product of the reflected radiation signal components.

62. An apparatus according to claim 61 wherein the reflected radiation signal components comprises signal components arising from radiation polarized at polarization angles which are substantially parallel, or substantially perpendicular, to the orientation of the feature.

63. A substrate processing method comprising:
   (a) placing a substrate in a process zone;
   (b) setting process conditions of an energized gas to process the substrate;

(c) providing a source of radiation in the process zone;

(d) detecting radiation that is reflected from a substrate during processing of the substrate and generating a signal; and (e) bandpass filtering the signal.

64. A method according to claim 63 wherein (e) comprises increasing the intensity of a signal component arising from the radiation reflected by a feature being processed on the substrate relative to other signal components.

65. A method according to claim 63 wherein (e) comprises selectively passing through frequencies in a frequency passband while reducing the intensity of other frequencies.

66. A method according to claim 63 wherein the frequency passband relates to an intensity modulation frequency of the radiation reflected from the feature being processed on the substrate.

67. A method according to claim 66 wherein the frequency passband is centered about the modulation frequency.

68. A method according to claim 63 comprising providing radiation polarized at one or more polarization angles that are selected in relation to an orientation of a feature being processed on the substrate.

69. A method according to claim 68 wherein the radiation is polarized at a plurality of polarization angles.

70. A method according to claim 68 wherein the one or more polarization angles comprise a polarization angle is substantially parallel, or substantially perpendicular, to the orientation of the feature.

71. A method according to claim 68 wherein the one or more polarization angles comprise a first polarization angle substantially parallel to the feature orientation and a second polarization angle substantially perpendicular to the feature orientation.

72. A method according to claim 71 wherein the feature is a trench having a principal orientation, and wherein the one or more polarization angles comprise a polarization angle that is related to the principal orientation of the trench.

73. A method according to claim 68 comprising processing signal components of reflected radiation that are polarized at the one or more polarization angles.

74. A method according to claim 73 comprising determining a ratio or subtraction product of the reflected radiation signal components.

75. A method according to claim 73 wherein the reflected radiation signal components comprises signal components arising from radiation polarized at polarization angles which are substantially parallel, or substantially perpendicular, to the orientation of the feature.

76. A substrate processing apparatus comprising:

a process chamber comprising a substrate support, gas inlet, gas energizer, gas exhaust, and a wall having a recess with a window therein and a mask over the window; and a process monitoring system capable of monitoring a process that may be conducted in the process chamber, through the window in the recess of the wall.

77. An apparatus according to claim 76 wherein the mask covers the window.

78. An apparatus according to claim 76 wherein the mask comprises one or more apertures sized to reduce the deposition of process residues therein.

79. An apparatus according to claim 78 wherein the apertures comprise an aspect ratio of at least about 0.25:1.

80. An apparatus according to claim 78 wherein the apertures comprise an aspect ratio of less than about 12:1.

81. An apparatus according to claim 78 wherein the apertures comprise an opening size of from about 0.1 to about 50 mm.

82. An apparatus according to claim 78 wherein the apertures comprise a depth of from about 0.5 to about 500 mm.

83. An apparatus according to claim 76 further comprising an electromagnetic field source adapted to maintain an electromagnetic field about the window.

84. An apparatus according to claim 83 wherein the electromagnetic field source comprises an electrical or magnetic field source.

85. An apparatus according to claim 76 wherein the process monitoring system comprises a radiation detector to detect a reflected radiation and generate a signal, and a filter to filter the signal.

86. An apparatus according to claim 76 further comprising a radiation polarizer.

87. A method of processing a substrate in a chamber, the method comprising:

placing the substrate in the chamber;

providing an energized gas in the chamber to process the substrate;

masking a window provided in a recess in a wall of the chamber; and monitoring a process that may be conducted in the chamber through the window in the recess in the wall.

88. A method according to claim 87 wherein masking the window comprises reducing deposition of process residues on the window.

89. A method according to claim 87 wherein masking the window comprises covering the window with a mask having one or more apertures.

90. A method according to claim 87 comprising maintaining an electromagnetic field about the window.

91. A method according to claim 90 comprising preferentially localizing the electromagnetic field about the window.

92. A method according to claim 87 comprising detecting a substrate reflected radiation, generating a signal, and a filtering the signal.

93. A method according to claim 92 comprising polarizing a radiation that is reflected from the substrate and detecting the radiation, and processing the signal.

94. A method according to claim 93 comprising polarizing the radiation to one or more polarization angles related to an orientation of a feature being processed on the substrate.

95. A substrate etching method comprising:

(a) placing a substrate in a process zone, the substrate having a first layer with an initial thickness;

(b) providing energized gas in the process zone to etch features in the first layer in the substrate, the features having a principal orientation;

(c) polarizing radiation at one or more of (i) a first polarization angle that is substantially parallel to the principal orientation of the features being etched on the substrate, and (ii) a second polarization angle that is substantially perpendicular to the principal orientation;

(d) directing the polarized radiation onto the substrate;

(e) detecting an intensity of the polarized radiation reflected from the substrate and generating a signal trace; and (f) evaluating the signal trace to identify a feature of the signal trace that occurs when a predetermined thickness of the first layer remains on the substrate to determine an endpoint of the process.

96. A method according to claim 95 comprising evaluating the signal trace relative to a stored trace or feature.

97. A method according to claim 95 comprising the initial steps of (1) determining a signal trace of an intensity of a reflected radiation from a substrate being etched, and (2) selecting the feature from the signal trace.

98. A substrate etching apparatus comprising:
(a) a chamber comprising a substrate support, gas supply, gas energizer, and gas exhaust; the chamber capable of maintaining an energized gas therein to etch features in the substrate, the features having a principal orientation;
(b) a radiation polarizer to polarize radiation to one or more of (i) a first polarization angle that is substantially parallel to the principal orientation of the features being etched in the substrate, and (ii) a second polarization angle that is substantially perpendicular to the principal orientation;
(c) a radiation detector to detect an intensity of the polarized radiation reflected from the substrate and generate a signal trace; and
(d) a controller to evaluate the signal trace to identify a feature of the signal trace that occurs when a predetermined thickness of the first layer remains on the substrate to determine an endpoint of the process.

99. An apparatus according to claim 98 wherein the controller evaluates the signal trace relative to a stored trace or feature.

* * * * *